United States Patent
Llinas-Brunet

(10) Patent No.: US 6,919,423 B2
(45) Date of Patent: Jul. 19, 2005

(54) HEPATITIS C INHIBITOR COMPOUND

(75) Inventor: Montse Llinas-Brunet, Dollard-des-Ormeaux (CA)

(73) Assignee: Boehringer Ingelheim International, GmbH, Ingelheim (DE)

(*) Notice: Subject to any disclaimer, the term of this patent is extended or adjusted under 35 U.S.C. 154(b) by 0 days.

(21) Appl. No.: 10/791,987

(22) Filed: Mar. 3, 2004

(65) Prior Publication Data

US 2004/0229818 A1 Nov. 18, 2004

Related U.S. Application Data

(60) Provisional application No. 60/452,281, filed on Mar. 5, 2003.

(51) Int. Cl.[7] .......................... A61K 38/16; A61K 38/00
(52) U.S. Cl. ............................................. 530/18; 514/2
(58) Field of Search ........................................ 514/18, 2

(56) References Cited

U.S. PATENT DOCUMENTS

| | | | |
|---|---|---|---|
| 6,323,180 B1 * | 11/2001 | Llinas-Brunet et al. ....... | 514/18 |
| 6,329,379 B1 * | 12/2001 | Llinas-Brunet et al. ..... | 514/256 |
| 6,410,531 B1 * | 6/2002 | Llinas-Brunet et al. .. | 514/235.5 |
| 6,420,380 B2 * | 7/2002 | Llinas-Brunet et al. ..... | 514/289 |
| 6,534,523 B1 | 3/2003 | Llinas-Brunet et al. | |
| 6,642,204 B2 * | 11/2003 | Llinas-Brunet et al. ....... | 514/18 |

FOREIGN PATENT DOCUMENTS

| | | |
|---|---|---|
| WO | WO 99/07733 A2 | 2/1999 |
| WO | WO 00/09543 A2 | 2/2000 |
| WO | WO 00/09558 A1 | 2/2000 |

* cited by examiner

*Primary Examiner*—Christopher Tate
*Assistant Examiner*—Thomas Heard
(74) *Attorney, Agent, or Firm*—Michael P. Morris; Philip I. Datlow

(57) ABSTRACT

Compounds of formula (I):

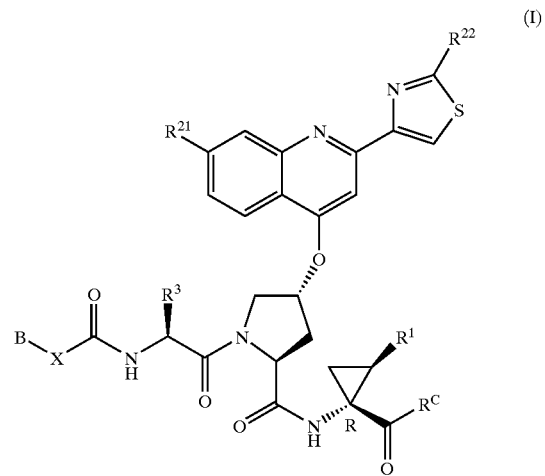

wherein B, X, $R^3$, $R^{21}$, $R^{22}$, $R^1$ and $R^c$ are defined herein. The compounds are useful as inhibitors of HCV NS3 protease.

38 Claims, No Drawings

HEPATITIS C INHIBITOR COMPOUND

This application claims benefit from U.S. Provisional Application No. 60/452,281, filed on Mar. 5, 2003, which application is herein incorporated by reference.

FIELD OF THE INVENTION

The present invention relates to compounds, processes for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulins treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy. Pegylated forms of interferons such as PEG-Intron® and Pegasys® can apparently partially address these deleterious side-effects but antiviral drugs still remain the avenue of choice for oral treatment of HCV.

Therefore, a need exists for the development of effective antiviral agents for treatment of HCV infection that overcome the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2–NS3 junction (henceforth referred to as NS2/3 protease); the second one is a serine protease contained within the N-terminal region of NS3 (NS3 protease) and mediates all the subsequent cleavages downstream of NS3, both in cis, at the NS3–NS4A cleavage site, and in trans, for the remaining NS4A–NS4B, NS4B–NS5A, NS5A–NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus.

In WO 00/09543, compounds of the formula

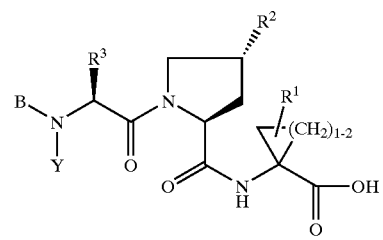

wherein a preferred meaning of $R^2$ is an unsubstituted or mono- or disubstituted quinolinyl residue as defined therein, are described as hepatitis C viral NS3 protease inhibitors, an enzyme essential for the replication of the hepatitis C virus.

The present invention provides tripeptide compounds that have improved potency against the HCV NS3 protease. Furthermore, compounds being highly active in cell culture are provided.

An advantage of one aspect of the present invention resides in the fact that compounds according to this invention specifically inhibit the NS3 protease and do not show significant inhibitory activity against other serine proteases such as human leukocyte elastase (HLE), porcine pancreatic elastase (PPE), or bovine pancreatic chymotrypsin, or cysteine proteases such as human liver cathepsin B (Cat B).

Furthermore, compounds according to this invention can achieve detectable blood plasma levels in pharmacokinetic experiments.

SUMMARY OF THE INVENTION

Included in the scope of the invention is a racemate, diastereoisomer, or optical isomer of a compound of formula (I):

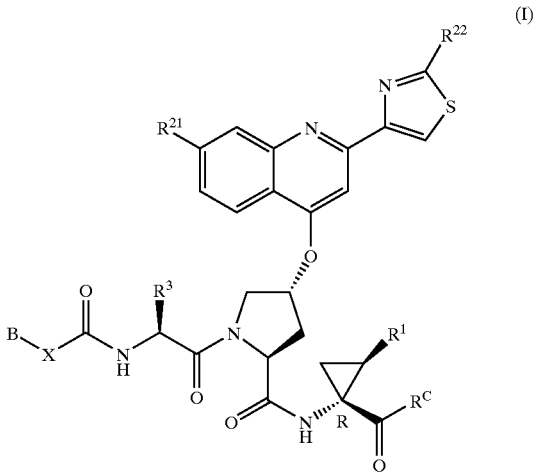

wherein
B is $(C_{1-10})$alkyl, $(C_{3-7})$cycloalkyl or $(C_{1-4})$alkyl-$(C_{3-7})$cycloalkyl,
 a) wherein said cycloalkyl and alkyl-cycloalkyl may be mono-, di- or tri-substituted with $(C_{1-3})$alkyl; and
 b) wherein said alkyl, cycloalkyl and alkyl-cycloalkyl may be mono- or di-substituted with substituents selected from hydroxy and O—$(C_{1-4})$alkyl; and
 c) wherein each of said alkyl-groups may be mono-, di- or tri-substituted by halogen; and
 d) wherein in each of said cycloalkyl-groups being 5-, 6- or 7-membered, one or two —$CH_2$-groups not being directly linked to each other may be replaced by —O— such that the O-atom is linked to the group X via at least two C-atoms;
X is O or NH;
$R^3$ is $(C_{2-8})$alkyl, $(C_{3-7})$cycloalkyl or $(C_{1-3})$alkyl-$(C_{3-7})$cycloalkyl, wherein each of said alkyl and cycloalkyl groups may be mono-, di- or tri-substituted with $(C_{1-4})$alkyl;
$R^{21}$ is H, halogen, —OH, $(C_{1-6})$alkyl, $(C_{3-6})$cycloalkyl, —$(C_{1-4})$alkyl-$(C_{3-6})$cycloalkyl, $(C_{1-6})$alkoxy, —O—$(C_{3-6})$cycloalkyl, —O—$(C_{1-4})$alkyl-$(C_{3-6})$cycloalkyl or —N$(R^{24})_2$, wherein each $R^{24}$ is independently: H, $(C_{1-6})$alkyl, —$(C_{3-6})$cycloalkyl, or —$(C_{1-4})$alkyl-$(C_{3-6})$cycloalkyl;
$R^{22}$ is —NR$^{N2}$COOR$^0$ or —NR$^{N2}$CONR$^{N3}$R$^{N1}$, wherein
 $R^0$ is selected from $(C_{1-8})$alkyl, $(C_{3-7})$cycloalkyl and $(C_{1-4})$alkyl-$(C_{3-7})$cycloalkyl, wherein said cycloalkyl and alkyl-cycloalkyl may be mono-, di- or tri-substituted with $(C_{1-3})$alkyl;
 $R^{N1}$ is H or $R^0$ as defined above; and
 $R^{N2}$ and $R^{N3}$ are independently selected from H and methyl;
$R^1$ is ethyl or vinyl;
$R^c$ is hydroxy or NHSO$_2$R$^S$ wherein R$^S$ is $(C_{1-6})$alkyl, $(C_{3-7})$cycloalkyl or $(C_{1-6})$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; each of which optionally being mono-, di- or tri-substituted with substituents selected from halogen, hydroxy, cyano, $(C_{1-4})$alkyl, O—$(C_{1-6})$alkyl, —CO—NH$_2$, —CO—NH($(C_{1-4})$alkyl), —CO—N($(C_{1-4})$alkyl)$_2$, —NH$_2$, —NH($(C_{1-4})$alkyl), —N($(C_{1-4})$alkyl)$_2$, wherein $(C_{1-4})$alkyl and O—$(C_{1-6})$alkyl are optionally mono-, di- or trisubstituted with halogen; and each of which optionally being monosubstituted with nitro;
or a pharmaceutically acceptable salt or ester thereof.

Included within the scope of this invention is a pharmaceutical composition comprising an anti-hepatitis C virally effective amount of a compound of formula I, or a pharmaceutically acceptable salt or ester thereof, in admixture with at least one pharmaceutically acceptable carrier medium or auxiliary agent.

According to a further aspect of this embodiment the pharmaceutical composition according to this invention comprises a therapeutically effective amount of at least one other antiviral agent. This other antiviral agent is preferably selected from another anti-HCV agent, HIV inhibitor, HAV inhibitor and HBV inhibitor.

Another important aspect of the invention involves a method of treating or preventing a hepatitis C viral infection in a mammal by administering to the mammal an anti-hepatitis C virally effective amount of a compound of formula I, a pharmaceutically acceptable salt or ester thereof, or a composition as described above, alone or in combination with at least one antiviral agent, administered together or separately.

Also within the scope of this invention is the use of a compound of formula I, or a pharmaceutically acceptable salt or ester thereof, as described herein, for the manufacture of a medicament for the treatment or prevention of hepatitis C viral infection in a mammal.

DETAILED DESCRIPTION OF PREFERRED EMBODIMENTS

Definitions

As used herein, the following definitions apply unless otherwise noted: With reference to the instances where (R) or (S) is used to designate the absolute configuration of a substituent or asymmetric center of a compound of formula I, the designation is done in the context of the whole compound and not in the context of the substituent or asymmetric center alone.

The designation "P1, P2, and P3" as used herein refer to the position of the amino acid residues starting from the C-terminus end of the peptide analogs and extending towards the N-terminus (i.e. P1 refers to position 1 from the C-terminus, P2: second position from the C-terminus, etc.) (see Berger A. & Schechter I., Transactions of the Royal Society London series B257, 249–264 (1970)).

As used herein the term "(1R, 2S)-vinyl-ACCA" refers to a compound of formula:

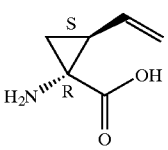

namely, (1R, 2S) 1-amino-2-ethenylcyclopropanecarboxylic acid.

The term "$(C_{1-n})$alkyl" as used herein, either alone or in combination with another substituent, means acyclic, straight or branched chain alkyl substituents containing from 1 to n carbon atoms. "$(C_{1-6})$alkyl" includes, but is not limited to, methyl, ethyl, n-propyl, n-butyl, 1-methylethyl (i-propyl), 1-methylpropyl, 2-methylpropyl, 1,1-dimethylethyl(tert-butyl), pentyl and hexyl. The abbreviation Me denotes a methyl group.

The term "$(C_{3-7})$cycloalkyl" as used herein, either alone or in combination with another substituent, means a cycloalkyl substituent containing from 3 to 7 carbon atoms and includes cyclopropyl, cyclobutyl, cyclopentyl, cyclohexyl and cycloheptyl.

The term "$(C_{1-n})$alkyl-$(C_{3-7})$cycloalkyl" as used herein means an alkylene radical containing 1 to n carbon atoms to which a cycloalkyl radical containing from 3 to 7 carbon atoms is directly linked; for example, cyclopropylmethyl, cyclopentylethyl, cyclohexylmethyl, cyclohexylethyl and cycloheptylpropyl.

The term "$C_6$ or $C_{10}$ aryl" as used herein, either alone or in combination with another radical, means either an aromatic monocyclic group containing 6 carbon atoms or an aromatic bicyclic group containing 10 carbon atoms. For example, aryl includes phenyl, 1-naphthyl or 2-naphthyl.

As used herein, the term "alkyl-aryl" means an alkyl radical to which an aryl is bonded. Examples of $(C_{1-3})$alkyl-aryl are benzyl(phenylmethyl), phenylethyl and phenylpropyl.

The term "O—$(C_{1-n})$alkyl" or "$(C_{1-n})$alkoxy" as used herein, either alone or in combination with another radical, means the radical —O—$(C_{1-n})$alkyl wherein alkyl is as defined above containing up to n carbon atoms, and includes methoxy, ethoxy, propoxy, 1-methylethoxy, butoxy and 1,1-dimethylethoxy. The latter radical is known commonly as tert-butoxy.

The term "halo" as used herein means a halogen substituent selected from fluoro, chloro, bromo or iodo.

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

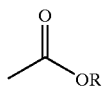

in which the R moiety of the ester is selected from alkyl (e.g. methyl, ethyl, n-propyl, tert-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters can be found in Design of prodrugs, Bundgaard, H. Ed. Elsevier (1985) incorporated herewith by reference. Such pharmaceutically acceptable esters are usually hydrolyzed in vivo when injected in a mammal and transformed into the acid form of the compound of formula I.

With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group.

In particular the esters may be a $C_{1-16}$ alkyl ester, an unsubstituted benzyl ester or a benzyl ester substituted with at least one halogen, $C_{1-4}$ alkyl, $C_{1-6}$ alkoxy, nitro or trifluoromethyl.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1–19.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethane-sulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "mammal" as it is used herein is meant to encompass humans, as well as non-human mammals which are susceptible to infection by hepatitis C virus including domestic animals, such as cows, pigs, horses, dogs and cats, and non-domestic animals.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Such agents can be selected from: another anti-HCV agent, HIV inhibitor, HAV inhibitor and HBV inhibitor. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as α-, β-, δ- and ω-interferons,τ-interferons, consensus interferons and asialo-interferons), class II interferons (such as γ-interferons) and pegylated interferons.

The term "inhibitor of HCV NS3 protease" as used herein means an agent (compound or biological) that is effective to inhibit the function of HCV NS3 protease in a mammal. Inhibitors of HCV NS3 protease include, for example, those compounds described in WO 99/07733, WO 99/07734, WO 00/09558, WO 00/09543, WO 00/59929, WO 03/064416, WO 03/064455, WO 03/064456, WO 02/060926, WO 03/053349, WO 03/099316 or WO 03/099274, and the Vertex pre-development candidate identified as VX-950.

The term "inhibitor of HCV polymerase" as used herein means an agent (compound or biological) that is effective to inhibit the function of an HCV polymerase in a mammal. This includes, for example, inhibitors of HCV NS5B polymerase. Inhibitors of HCV polymerase include non-nucleosides, for example, those compounds described in:

U.S. Application No. 60/441,674 filed Jan. 22, 2003, herein incorporated by reference in its entirety (Boehringer Ingelheim), U.S. Application No. 60/441,871 filed Jan. 22, 2003, herein incorporated by reference in its entirety (Boehringer Ingelheim), U.S. application Ser. No. 10/198,680 filed 18 Jul. 2002, herein incorporated by reference in its entirety, which corresponds to WO 03/010140 (Boehringer Ingelheim), U.S. application Ser. No. 10/198,384 filed 18 Jul. 2002, herein incorporated by reference in its entirety, which corresponds to WO 03/010141 (Boehringer Ingelheim), U.S. application Ser. No. 10/198,259 filed 18 Jul. 2002, herein incorporated by reference in its entirety, which corresponds to WO 03/007945 (Boehringer Ingelheim), WO 03/026587 (Bristol Myers Squibb);

WO 02/100846 A1 and WO 02/100851 A2 (both Shire),

WO 01/85172 A1 and WO 02/098424 A1 (both GSK),

WO 00/06529 and WO 02/06246 A1 (both Merck),

WO 01/47883 and WO 03/000254 (both Japan Tobacco) and

EP 1 256 628 A2 (Agouron).

Furthermore other inhibitors of HCV polymerase also include nucleoside analogs, for example, those compounds described in:

WO 01/90121 A2 (Idenix);

WO 02/069903 A2 (Biocryst Pharmaceuticals Inc.), and

WO 02/057287 A2 and WO 02/057425 A2 (both Merck/Isis).

Specific examples of inhibitors of an HCV polymerase, include JTK-002/003 and JTK-109 (Japan Tobacco) and NM-283 (Idenix).

The term "inhibitor of another target in the HCV life cycle" as used herein means an agent (compound or biological) that is effective to inhibit the formation and/or replication of HCV in a mammal other than by inhibiting the function of the HCV NS3 protease. This includes agents that interfere with either host or HCV viral mechanisms necessary for the formation and/or replication of HCV in a mammal. Inhibitors of another target in the HCV life cycle include, for example, agents that inhibit a target selected from helicase, NS2/3 protease and internal ribosome entry site (IRES). Specific examples of inhibitors of another target in the HCV life cycle include ISIS-14803 (ISIS Pharmaceuticals).

The term "HIV inhibitor" as used herein means an agents (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleoside inhibitors, non-nucleoside inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include $\alpha$-, $\beta$-, $\delta$-, $\omega$ interferons, $\tau$-interferons, consensus interferons, asialo-interferons and pegylated forms thereof.

The term "class II interferon" as used herein means an interferon selected from a group of interferons that all bind to receptor type II. Examples of class II interferons include $\gamma$-interferons.

Specific preferred examples of some of these agents are listed below:

antiviral agents: ribavirin and amantadine;
immunomodulatory agents: class I interferons, class II interferons and pegylated interferons;
HCV polymerase inhibitors: nucleoside analogs and non-nucleosides;
inhibitor of another target in the HCV life cycle that inhibits a target selected from: NS3 helicase, NS2/3 protease or internal ribosome entry site (IRES);
HIV inhibitors: nucleosidic inhibitors, non-nucleosidic inhibitors, protease inhibitors, fusion inhibitors and integrase inhibitors; or
HBV inhibitors: agents that inhibit viral DNA polymerase or is an HBV vaccine.

As discussed above, combination therapy is contemplated wherein a compound of formula (1), or a pharmaceutically acceptable salt thereof, is co-administered with at least one additional agent selected from: an antiviral agent, an immunomodulatory agent, another inhibitor of HCV NS3 protease, an inhibitor of HCV polymerase, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (1), or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, in order to prevent the appearance of symptoms of the disease in the individual.

The following sign - - - is used in sub-formulas to indicate the bond, which is connected to the rest of the molecule as defined.

Preferred Embodiments

In the following preferred embodiments, groups and substituents of the compounds according to this invention are described in detail.

B is preferably selected from $(C_{2-8})$alkyl, $(C_{3-7})$cycloalkyl and $(C_{1-3})$alkyl-$(C_{3-7})$cycloalkyl,
a) wherein said cycloalkyl and alkyl-cycloalkyl may be mono-, di- or tri-substituted with $(C_{1-3})$alkyl; and
b) wherein said alkyl, cycloalkyl and alkyl-cycloalkyl may be mono- or di-substituted with hydroxy or O—$(C_{1-4})$alkyl; and
c) wherein each of said alkyl-groups may be mono-, di- or tri-substituted with fluorine or mono-substituted by chlorine or bromine, and
d) wherein in each of said cycloalkyl-groups being 5-, 6- or 7-membered, one or two —$CH_2$-groups not being directly linked to each other may be replaced by —O-such that the O-atom is linked to the group X via at least two C-atoms.

More preferably B is selected from ethyl, n-propyl, i-propyl, n-butyl, 1-methylpropyl, 2-methylpropyl, tert-butyl, cyclopropyl, cyclobutyl, cyclopentyl, cyclohexyl, cyclopropylmethyl, cyclobutylmethyl, cyclopentylmethyl and cyclohexylmethyl,
a) wherein each of said cycloalkyl and alkyl-cycloalkyl groups optionally being substituted by 1 to 3 substituents selected from methyl and ethyl;
b) wherein each of said groups optionally being mono- or di-substituted with substituents selected from hydroxy, methoxy and ethoxy; and
c) wherein each of said alkyl groups may be mono-, di- or tri-substituted with fluorine or mono-substituted by chlorine or bromine; and
d) wherein in each of said cycloalkyl-groups being 5-, 6- or 7-membered, one or two —$CH_2$-groups not being directly linked to each other may be replaced by —O-such that the O-atom is linked to the group X via at least two C-atoms.

B is most preferably selected from ethyl, 1-methylethyl, 1,1-dimethylethyl, propyl, 1-methylpropyl, 2-methylpropyl, 1,1-dimethylpropyl, 1,2-dimethylpropyl, 2,2-dimethylpropyl, 1,2,2-trimethylpropyl, 1-ethylpropyl, 1-ethyl-2-methylpropyl, 1-(1-methylethyl)-2-methylpropyl, 1-ethyl-2,2-dimethylpropyl, butyl, 1-methylbutyl, 2-methylbutyl, 3-methylbutyl, 1,2-dimethylbutyl, 1,1-dimethylbutyl, 1,3-dimethylbutyl, 2,2-dimethylbutyl, 2,3-dimethylbutyl, 3,3-dimethylbutyl, 1,2,2-trimethylbutyl, 1,2,3-trimethylbutyl, 2,2,3-trimethylbutyl, 2,3,3-trimethylbutyl and 2,2,3-trimethylbutyl, whereby these alkyl-groups may be substituted with chlorine or bromine or 1, 2 or 3 fluorine substituents. Examples of preferred fluorinated alkyl groups are 2-fluoroethyl and 3,3,3-trifluoropropyl.

Furthermore most preferably, B is cyclopropyl, cyclobutyl, cyclopentyl, cyclohexyl, cyclopropylmethyl, cyclobutylmethyl, cyclopentylmethyl and cyclohexylmethyl; optionally substituted with one or two methyl substituents.

Most preferably B is selected from cyclopropyl, cyclobutyl, cyclopentyl, cyclohexyl, 1-methylcyclopentyl and 1-methylcyclohexyl.

Even most preferably B is selected from cyclobutyl, cyclopentyl and cyclohexyl.

In addition, most preferably B is selected from the following formulas, wherein a CH$_2$-group of a cycloalkyl group is replaced by oxygen:

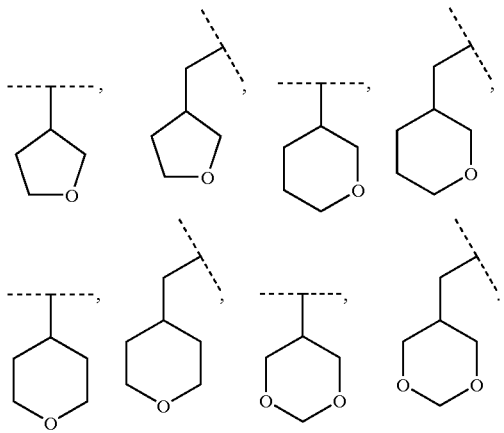

The above listed cycloalkyl and alkyl-cycloalkyl groups, optionally comprising 1 or 2 O-atoms, are optionally substituted by 1, 2 or 3 methyl-groups. Especially those cycloalkyl groups, optionally comprising 1 or 2 O-atoms, are preferred, wherein the α-C-atom is substituted with methyl.

Examples of preferred substituted cyclic groups are

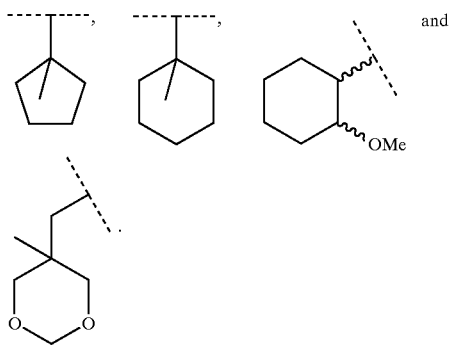

According to one embodiment of this invention X is O.

According to another embodiment of this invention X is NH.

R$^3$ is preferably selected from ethyl, propyl, butyl, cyclopropyl, cyclobutyl, cyclopentyl, cyclohexyl, cyclopropylmethyl, cyclobutylmethyl, cyclopentylmethyl and cyclohexylmethyl, each of which optionally being substituted by 1 to 3 substituents selected from methyl, ethyl and propyl.

More preferably R$^3$ is selected from 1-methylethyl, 1,1-dimethylethyl, 1-methylpropyl, 2-methylpropyl, 1,1-dimethylpropyl, 1,2-dimethylpropyl, 2,2-dimethylpropyl, cyclopentyl, cyclohexyl, 1-methyl-cyclopentyl, 1-methyl-cyclohexyl, cyclopentylmethyl, cyclohexylmethyl, (1-methyl-cyclopentyl)-methyl and (1-methyl-cyclohexyl)-methyl.

R$^3$ is most preferably selected from 1,1-dimethylethyl, cyclopentyl, cyclohexyl and 1-methylcyclohexyl.

R$^3$ is even most preferably selected from 1,1-dimethylethyl and cyclohexyl.

The substituent R$^{21}$ is preferably selected from halogen, —OH, (C$_{1-3}$)alkoxy or N(R$^{24}$)$_2$, wherein each R$^{24}$ is independently: H or (C$_{1-6}$)alkyl.

More preferably R$^{21}$ is selected from —OH, —OCH$_3$ and —N(CH$_3$)$_2$, wherein —OCH$_3$ and —N(CH$_3$)$_2$ is the most preferred definition. Even most preferably, R$^{21}$ is —OCH$_3$.

The substituent R$^{22}$ is preferably defined as —NHCOOR$^O$ or —NHCONHR$^{N1}$, wherein R$^{N1}$ and R$^O$ are defined as hereinbefore or hereinafter. More preferably, R$^{22}$ is defined as —NHCOOR$^O$.

According to a preferred embodiment R$^O$ and R$^{N1}$ are selected from the group consisting of methyl, ethyl, propyl, 1-methylethyl, butyl, 1-methylpropyl, 2-methylpropyl, 1,1-dimethylethyl, cyclopropyl, cyclobutyl, cyclopentyl, cyclohexyl, cyclopropylmethyl, cyclobutylmethyl, cyclopentylmethyl, and cyclohexylmethyl, wherein said cycloalkyl and alkyl-cycloalkyl groups are unsubstituted or substituted with 1 to 3 substituents selected from methyl and ethyl.

Most preferably herein R$^O$ and R$^{N1}$ are independently selected from ethyl, 1-methylethyl and cyclopentyl.

In the moiety P1 the substituent R$^1$ and the carbonyl take a syn orientation. Therefore, in the case R$^1$ is ethyl, the asymmetric carbon atoms in the cyclopropyl group take the R,R configuration according to the subformula:

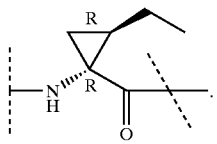

In the case R$^1$ is vinyl, the asymmetric carbon atoms in the cyclopropyl group take the R,S configuration according to the subformula:

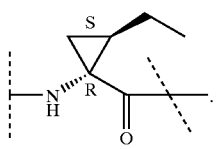

R$^1$ is preferably vinyl.

R$^c$ is preferably selected from hydroxy or NHSO$_2$R$^S$ wherein R$^S$ is methyl, ethyl, n-propyl, i-propyl, n-butyl, 1-methylpropyl, 2-methylpropyl, tert-butyl, cyclopropyl, cyclobutyl, cyclopentyl, cyclohexyl, cyclopropylmethyl, cyclobutylmethyl, cyclopentylmethyl, cyclohexylmethyl, phenyl, naphthyl, pyridinyl, phenylmethyl(benzyl), naphthylmethyl or pyridinylmethyl;

a) each of which optionally being mono-, di- or tri-substituted with substituents selected from fluorine and methyl; and
b) each of which optionally being mono- or disubstituted with substituents selected from hydroxy, trifluoromethyl, methoxy and trifluoromethoxy; and
c) each of which optionally being monosubstituted with substituents selected from chlorine, bromine, cyano, nitro, —CO—NH$_2$, —CO—NHCH$_3$, —CO—N(CH$_3$)$_2$, —NH$_2$, —NH(CH$_3$) and —N(CH$_3$)$_2$.

Most preferably, $R^c$ is hydroxy, NHSO$_2$-methyl, NHSO$_2$-ethyl, NHSO$_2$-(1-methyl)ethyl, NHSO$_2$-propyl, NHSO$_2$-cyclopropyl, NHSO$_2$-cyclopropylmethyl, NHSO$_2$-cyclobutyl, NHSO$_2$-cyclopentyl or NHSO$_2$-phenyl.

According to a most preferred embodiment, the group $R^c$ is hydroxy. According to an alternative most preferred embodiment, the group $R^c$ is NHSO$_2$-cyclopropyl.

According to a preferred embodiment of this invention, compounds are represented by formula:

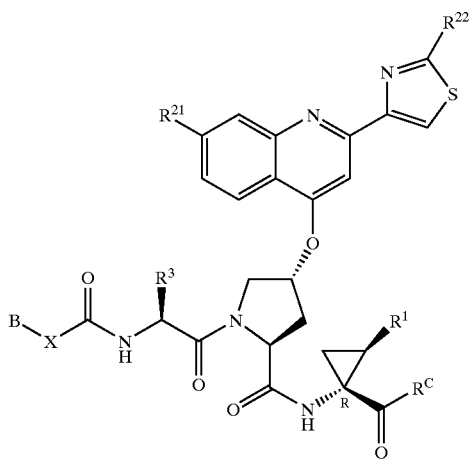

wherein
B is (C$_{1-10}$)alkyl, (C$_{3-7}$)cycloalkyl or (C$_{1-4}$)alkyl-(C$_{3-7}$)cycloalkyl,
  a) wherein said cycloalkyl and alkyl-cycloalkyl may be mono-, di- or tri-substituted with (C$_{1-3}$)alkyl; and
  b) wherein said alkyl, cycloalkyl and alkyl-cycloalkyl may be mono- or di-substituted with substituents selected from hydroxy and O—(C$_{1-4}$)alkyl; and
  c) wherein all said alkyl-groups may be mono-, di- or tri-substituted by halogen; and
  d) wherein in all said cycloalkyl-groups being 5-, 6- or 7-membered, one or two —CH$_2$-groups not being directly linked to each other may be replaced by —O— such that the O-atom is linked to the group X via at least two C-atoms;
X is O or NH;
$R^3$ is (C$_{2-8}$)alkyl, (C$_{3-7}$)cycloalkyl or (C$_{1-3}$)alkyl-(C$_{3-7}$)cycloalkyl, wherein said cycloalkyl groups may be mono-, di- or tri-substituted with (C$_{1-4}$)alkyl;
$R^{21}$ H, halogen, —OH, (C$_{1-6}$)alkyl, (C$_{3-6}$)cycloalkyl, —(C$_{1-4}$)alkyl-(C$_{3-6}$)cycloalkyl, (C$_{1-6}$)alkoxy, —O—(C$_{3-6}$)cycloalkyl, —O—(C$_{1-4}$)alkyl-(C$_{3-6}$)cycloalkyl or —N(R$^{24}$)$_2$, wherein each R$^{24}$ is independently: H, (C$_{1-6}$)alkyl, —(C$_{3-6}$)cycloalkyl, or —(C$_{1-4}$)alkyl-(C$_{3-6}$)cycloalkyl;
$R^{22}$ is —NR$^{N2}$COOR$^0$ or —NR$^{N2}$CONR$^{N3}$R$^{N1}$ wherein
  R$^0$ is selected from (C$_{1-8}$)alkyl, (C$_{3-7}$)cycloalkyl and (C$_{1-4}$)alkyl-(C$_{3-7}$)cycloalkyl, wherein said cycloalkyl, alkyl-cycloalkyl may be mono-, di- or tri-substituted with (C$_{1-3}$)alkyl;
  R$^{N1}$ is H or R$^0$ as defined above; and
  R$^{N2}$ and R$^{N3}$ are independently selected from H and methyl;
$R^1$ is ethyl or vinyl;
$R^c$ is hydroxy or NHSO$_2$R$^S$ wherein R$^S$ is (C$_{1-6}$)alkyl, (C$_{3-7}$)cycloalkyl or (C$_{1-6}$)alkyl-(C$_{3-7}$)cycloalkyl, phenyl, naphthyl, pyridinyl, (C$_{1-4}$)alkyl-phenyl, (C$_{1-4}$)alkyl-naphthyl or (C$_{1-4}$)alkyl-pyridinyl; all of which optionally being mono-, di- or tri-substituted with substituents selected from halogen, hydroxy, cyano, (C$_{1-4}$)alkyl, O—(C$_{1-6}$)alkyl, —CO—NH$_2$, —CO—NH((C$_{1-4}$)alkyl), —CO—N((C$_{1-4}$)alkyl)$_2$, —NH$_2$, —NH((C$_{1-4}$)alkyl), —N((C$_{1-4}$)alkyl)$_2$; and all of which optionally being monosubstituted with nitro;
or a pharmaceutically acceptable salt or ester thereof.

According to another preferred embodiment of this invention, compounds are represented by formula:

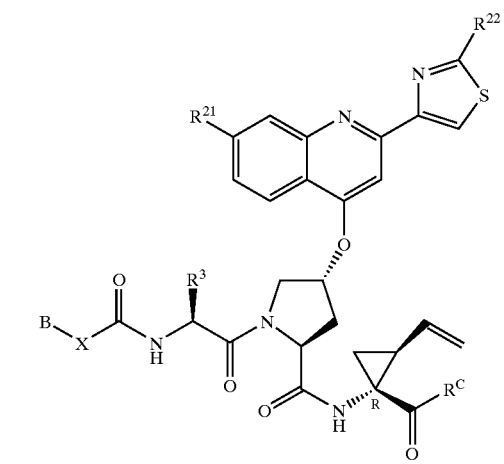

wherein $R^{21}$ is —OCH$_3$ or N(CH$_3$)$_2$;
$R^{22}$ is —NHCOOR$^0$ or —NHCONHR$^{N1}$, wherein
  R$^0$ and R$^{N1}$ is each independently selected from (C$_{1-4}$)alkyl or (C$_{3-6}$)cycloalkyl;
B is (C$_{4-6}$)cycloalkyl;
X is O or NH;
$R^3$ is tert-butyl or cyclohexyl;
$R^C$ is hydroxy or NHSO$_2$R$^S$ wherein R$^S$ is (C$_{1-4}$)alkyl, (C$_{3-6}$)cycloalkyl or phenyl;
or a pharmaceutically acceptable salt or ester thereof.
Preferably, $R^{21}$ is —OCH$_3$; $R^{22}$ is —NHCOOR$^0$ wherein R$^0$ is isopropyl or cyclopentyl; and R$^s$ is, cyclopropyl.
Also preferably, $R^C$ is hydroxy. More preferably, $R^{21}$ is —OCH$_3$; $R^{22}$ is —NHCOOR$^0$ wherein R$^0$ is isopropyl or cyclopentyl and $R^c$ is hydroxy.

Examples of preferred compounds according to this invention are listed in the following Tables 1 and 2.

According to an alternate embodiment, the pharmaceutical composition of this invention may additionally comprise at least one other anti-HCV agent. Examples of anti-HCV agents include, α-(alpha), β-(beta), δ-(delta), γ-(gamma), ω-(omega) and τ-(tau) interferon, pegylated α-interferon, ribavirin and amantadine.

According to another alternate embodiment, the pharmaceutical composition of this invention may additionally comprise at least one other inhibitor of HCV NS3 protease.

According to another alternate embodiment, the pharmaceutical composition of this invention may additionally comprise at least one inhibitor of HCV polymerase.

According to yet another alternate embodiment, the pharmaceutical composition of this invention may additionally comprise at least one inhibitor of other targets in the HCV life cycle, including but not limited to, helicase, NS2/3 protease or internal ribosome entry site (IRES).

The pharmaceutical composition of this invention may be administered orally, parenterally or via an implanted reservoir. Oral administration or administration by injection is preferred. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19th Ed. Mack Publishing Company, Easton, Pa., (1995).

Dosage levels of between about 0.01 and about 100 mg/kg body weight per day, preferably between about 0.1 and about 50 mg/kg body weight per day of the protease inhibitor compound described herein are useful in a monotherapy for the prevention and treatment of HCV mediated disease. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the composition of this invention comprises a combination of a compound of formula I, including a pharmaceutically acceptable salt or ester thereof, and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts and esters are formulated together with a pharmaceutically acceptable carrier, the resulting composition may be administered in vivo to mammals, such as man, to inhibit HCV NS3 protease or to treat or prevent HCV virus infection. Such treatment may also be achieved using a compound of this invention in combination with another antiviral agent. Preferred other antiviral agents are described within the Definitions section and the section of preferred pharmaceutical compositions according to this invention and include, but are not limited to: α-, β-, δ-, ω-, γ- and τ-interferon, ribavirin, amantadine; other inhibitors of HCV NS3 protease; inhibitors of HCV polymerase; inhibitors of other targets in the HCV life cycle, which include but not limited to, helicase, NS2/3 protease, or internal ribosome entry site (IRES); or combinations thereof. The additional agents may be combined with compounds of this invention to create a single dosage form. Alternatively these additional agents may be separately administered to a mammal as part of a multiple dosage form.

Accordingly, another embodiment of this invention provides a method of inhibiting HCV NS3 protease activity in a mammal by administering a compound of the formula I, including a pharmaceutically acceptable salt or ester thereof.

In a preferred embodiment, this method is useful in decreasing the NS3 protease activity of the hepatitis C virus infecting a mammal.

As discussed above, combination therapy is contemplated wherein a compound of formula (I), or a pharmaceutically acceptable salt or ester thereof, is co-administered with at least one additional antiviral agent. Preferred antiviral agents are described hereinbefore and examples of such agents are provided in the Definitions section. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt or ester thereof.

A compound of formula (I), or a pharmaceutically acceptable salt or ester thereof, set forth herein may also be used as a laboratory reagent. Furthermore a compound of this invention, including a pharmaceutically acceptable salt or ester thereof, may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

A compound of formula (I), including a pharmaceutically acceptable salt or ester thereof, set forth herein may also be used as a research reagent. A compound of formula (I), including a pharmaceutically acceptable salt or ester thereof, may also be used as positive control to validate surrogate cell-based assays or in vitro or in vivo viral replication assays.

Methodology

The compounds of the present invention are synthesized according to a general process as illustrated in Scheme I (wherein CPG is a carboxyl protecting group and APG is an amino protecting group):

Scheme I

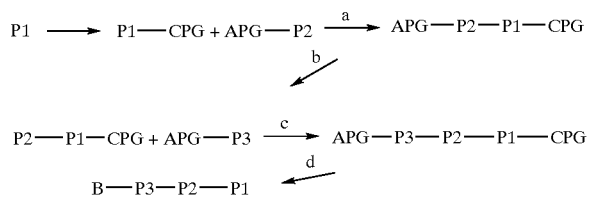

Briefly, the P1, P2, and P3 groups can be linked by well known peptide coupling techniques. The P1, P2, and P3 groups may be linked together in any order as long as the final compound corresponds to peptides of Formula (I). For example, P3 can be linked to P2-P1; or P1 linked to P3-P2.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I, or by solid phase peptide synthesis according to the method originally described in Merrifield, J. Am. Chem. Soc., (1963), 85, 2149–2154.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole. These coupling reactions can be performed in either solution (liquid phase) or solid phase.

More explicitly, the coupling step involves the dehydrative coupling of a free carboxyl of one reactant with the free amino group of the other reactant in the presence of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the presence of 1-hydroxybenzotriazole. Another practical and useful coupling agent is commercially available 2-(1H-benzotriazol-1-yl)-N,N, N',N'-tetramethyluronium tetrafluoroborate. Still another practical and useful coupling agent is commercially available O-(7-azabenzotriazol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine or N-methylpyrrolidine, is added to maintain the reaction mixture at a pH of about 8. The reaction temperature usually ranges between 0° C. and 50° C. and the reaction time usually ranges between 15 min and 24 h.

When a solid phase synthetic approach is employed, the C-terminal carboxylic acid is attached to an insoluble carrier (usually polystyrene). These insoluble carriers contain a group that will react with the carboxylic group to form a bond that is stable to the elongation conditions but readily cleaved later. Examples of which are: chloro- or bromomethyl resin, hydroxymethyl resin, trityl resin and 2-methoxy-4-alkoxy-benzylalcohol resin.

Many of these resins are commercially available with the desired C-terminal amino acid already incorporated: Alternatively, the amino acid can be incorporated on the solid support by known methods (Wang, S.-S., J. Am. Chem. Soc., (1973), 95, 1328; Atherton, E.; Shepard, R. C. "Solid-phase peptide synthesis; a practical approach" IRL Press: Oxford, (1989); 131–148). In addition to the foregoing, other methods of peptide synthesis are described in Stewart and Young, "Solid Phase Peptide Synthesis", $2^{nd}$ ed., Pierce Chemical Co., Rockford, Ill. (1984); Gross, Meienhofer, Udenfriend, Eds., "The Peptides: Analysis, Synthesis, Biology", Vol. 1, 2, 3, 5, and 9, Academic Press, New-York, (1980–1987); Bodansky et al., "The Practice of Peptide Synthesis" Springer-Verlag, New-York (1984).

The functional groups of the constituent amino acids generally must be protected during the coupling reactions to avoid formation of undesired bonds. The protecting groups that can be used are listed in Greene et al., "Protective Groups in Organic Synthesis", John Wiley & Sons, New York (1991) and "The Peptides: Analysis, Synthesis, Biology", Vol. 3, Academic Press, New York (1981).

The α-carboxyl group of the C-terminal residue is usually protected as an ester (CPG) that can be cleaved to give the carboxylic acid. Protecting groups that can be used include: 1) alkyl esters such as methyl, trimethylsilylethyl and tert-butyl, 2) aralkyl esters such as benzyl and substituted benzyl, or 3) esters that can be cleaved by mild base treatment or mild reductive means such as trichloroethyl and phenacyl esters.

The α-amino group of each amino acid to be coupled to the growing peptide chain must be protected (APG). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl. The preferred α-amino protecting group is either Boc or Fmoc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (RT) usually 20–22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting group are suitable: p-toluenesulfonyl(tosyl) moieties can be used to protect the amino side chain of amino acids such as Lys and Arg; acetamidomethyl, benzyl (Bn), or tert-butylsulfonyl moieties can be used to protect the sulfide-containing side chain of cysteine; benzyl (Bn) ethers can be used to protect the hydroxy-containing side chains of serine, threonine or hydroxyproline; and benzyl esters can be used to protect the carboxy-containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. The triphenylmethyl(trityl) moiety can be used to protect the sulfide-containing side chain of cysteine.

Once the elongation of the peptide is completed, all of the protecting groups are removed. When a liquid phase synthesis is used, the protecting groups are removed in whatever manner is dictated by the choice of protecting groups. These procedures are well known to those skilled in the art.

When a solid phase synthesis is used, the peptide is cleaved from the resin simultaneously with the removal of the protecting groups. When the Boc protection method is used in the synthesis, treatment with anhydrous HF containing additives such as dimethyl sulfide, anisole, thioanisole, or p-cresol at 0° C. is the preferred method for cleaving the peptide from the resin. The cleavage of the peptide can also be accomplished by other acid reagents such as trifluoromethanesulfonic acid/trifluoroacetic acid mixtures. If the Fmoc protection method is used, the N-terminal Fmoc group is cleaved with reagents described earlier. The other protecting groups and the peptide are cleaved from the resin using solution of trifluoroacetic acid and various additives such as anisole, etc.

In general, the compounds of formula I, and intermediates therefore, are prepared by known methods using reaction conditions which are known to be suitable for the reactants. Several such methods are disclosed in WO 00/09543, WO 00/09558 and U.S. Pat. No. 6,323,180.

The following schemes illustrate convenient processes using known methods for preparing the compounds of formula 1 when $R^c$ is OH and $R^1$ is vinyl.

Scheme II:

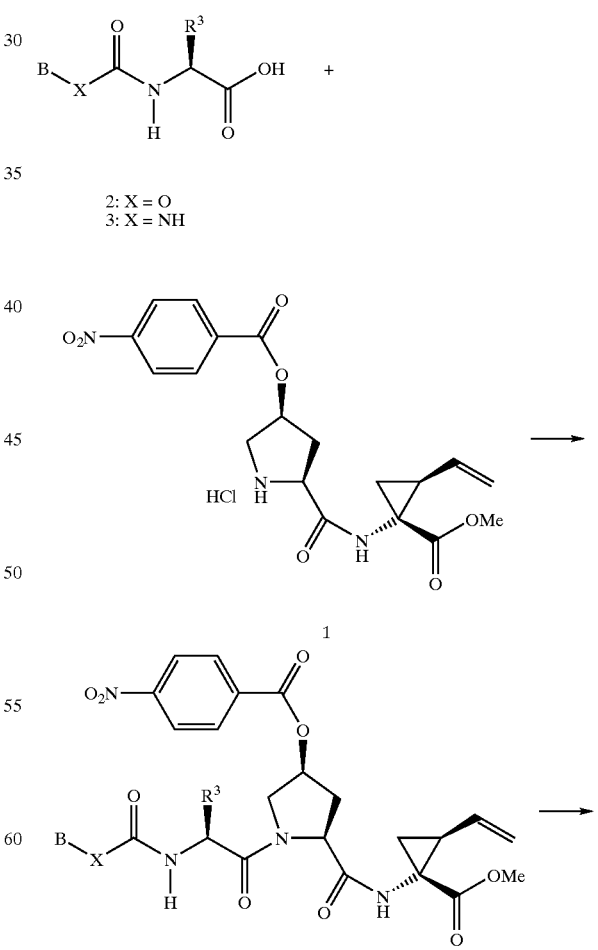

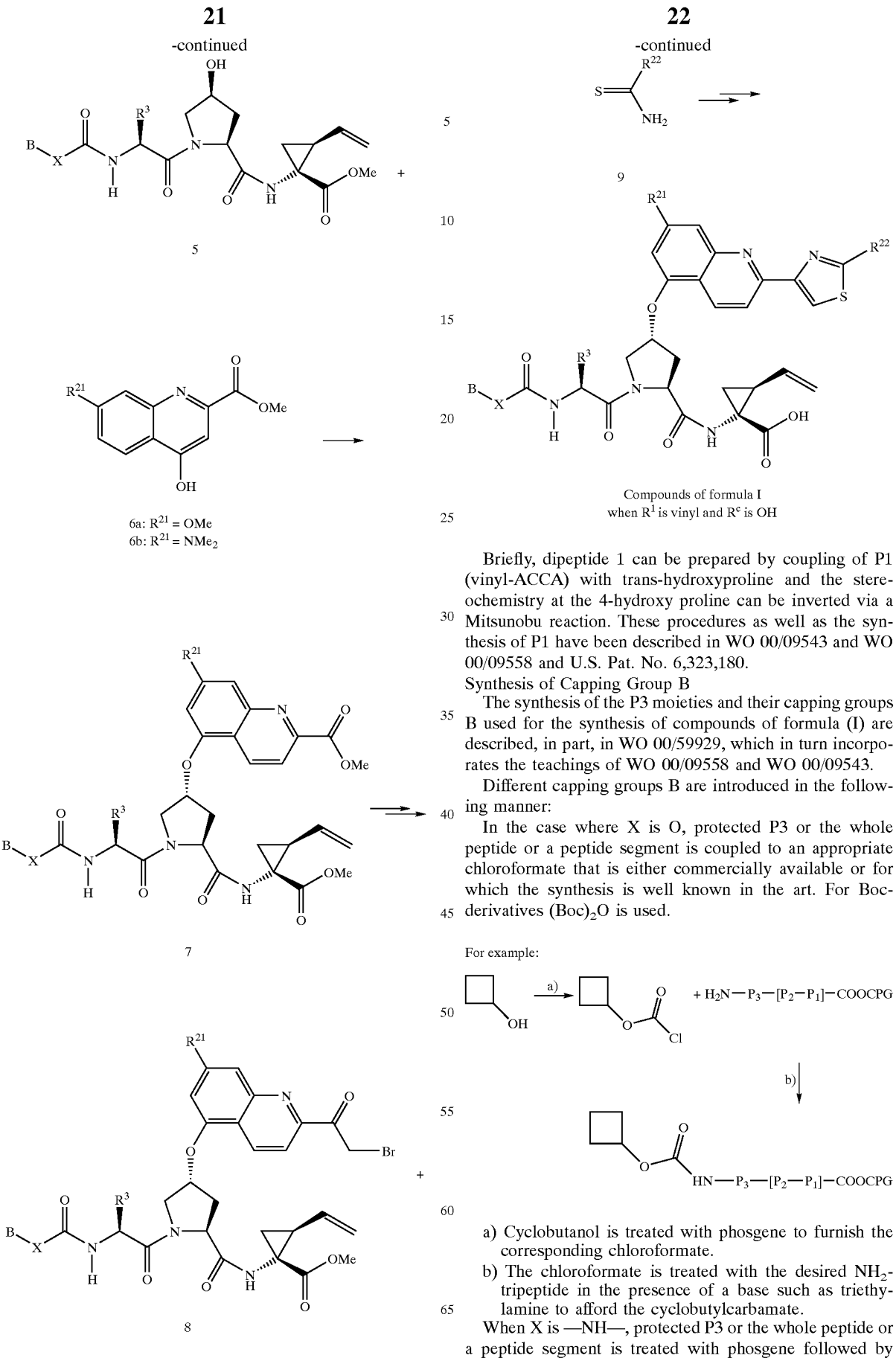

Briefly, dipeptide 1 can be prepared by coupling of P1 (vinyl-ACCA) with trans-hydroxyproline and the stereochemistry at the 4-hydroxy proline can be inverted via a Mitsunobu reaction. These procedures as well as the synthesis of P1 have been described in WO 00/09543 and WO 00/09558 and U.S. Pat. No. 6,323,180.

Synthesis of Capping Group B

The synthesis of the P3 moieties and their capping groups B used for the synthesis of compounds of formula (I) are described, in part, in WO 00/59929, which in turn incorporates the teachings of WO 00/09558 and WO 00/09543.

Different capping groups B are introduced in the following manner:

In the case where X is O, protected P3 or the whole peptide or a peptide segment is coupled to an appropriate chloroformate that is either commercially available or for which the synthesis is well known in the art. For Boc-derivatives (Boc)$_2$O is used.

For example:

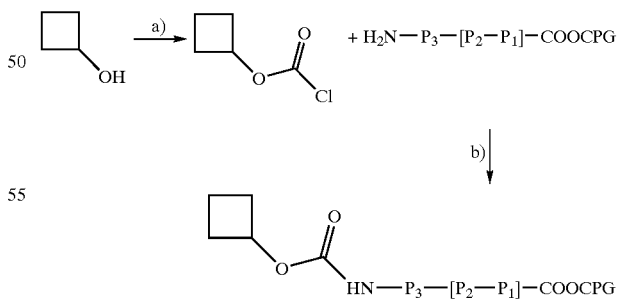

a) Cyclobutanol is treated with phosgene to furnish the corresponding chloroformate.
b) The chloroformate is treated with the desired NH$_2$-tripeptide in the presence of a base such as triethylamine to afford the cyclobutylcarbamate.

When X is —NH—, protected P3 or the whole peptide or a peptide segment is treated with phosgene followed by amine as described in SynLeft. February 1995; (2); 142–144. Alternatively the whole peptide or a peptide segment is treated with an alkyl isocyanate.

Synthesis of P2 Substituents:

The synthesis of 2-carbomethoxy-4-hydroxy-7-methoxyquinoline 6a and 2-carbomethoxy-7-dimethylamino-4-hydroxyquinoline 6b are described in WO 00/59929, which in turn incorporates the teachings of WO 00/09558 and WO 00/09543.

4-hydroxy-2-carbomethoxyquinoline derivatives are introduced in the tripeptide via a Mitsunobu reaction (Mitsunobu (1981), Synthesis, January, 1–28; Rano et al., (1995), Tet. Left. 36(22), 3779–3792; Krchnak et al., (1995), Tet. Left. 36(5), 62193–6196; Richter et al., (1994), Tet. Left. 35(27), 4705–4706). Tripeptides 7 can be converted to the desired compounds by first converting the 2-carbomethoxy group into a bromoketone via the diazoketone intermediate as shown in the examples and the final convertion into the aminothiazole is done by condensing bromo ketones 8 with the required thioureas 9. Final hydrolysis of the methyl ester is achieved by treatment with LiOH in methanol.

Alternatively, instead of substituted thioureas 9, the reaction can be performed with commercially available thiourea giving the corresponding unsubstituted aminothiazole which can be reacted with any chloroformate to give the corresponding thiazolyl carbamate derivative or with any alkyl-isocyanate to give the corresponding thiazolyl urea derivative as shown in scheme III.

Scheme III:

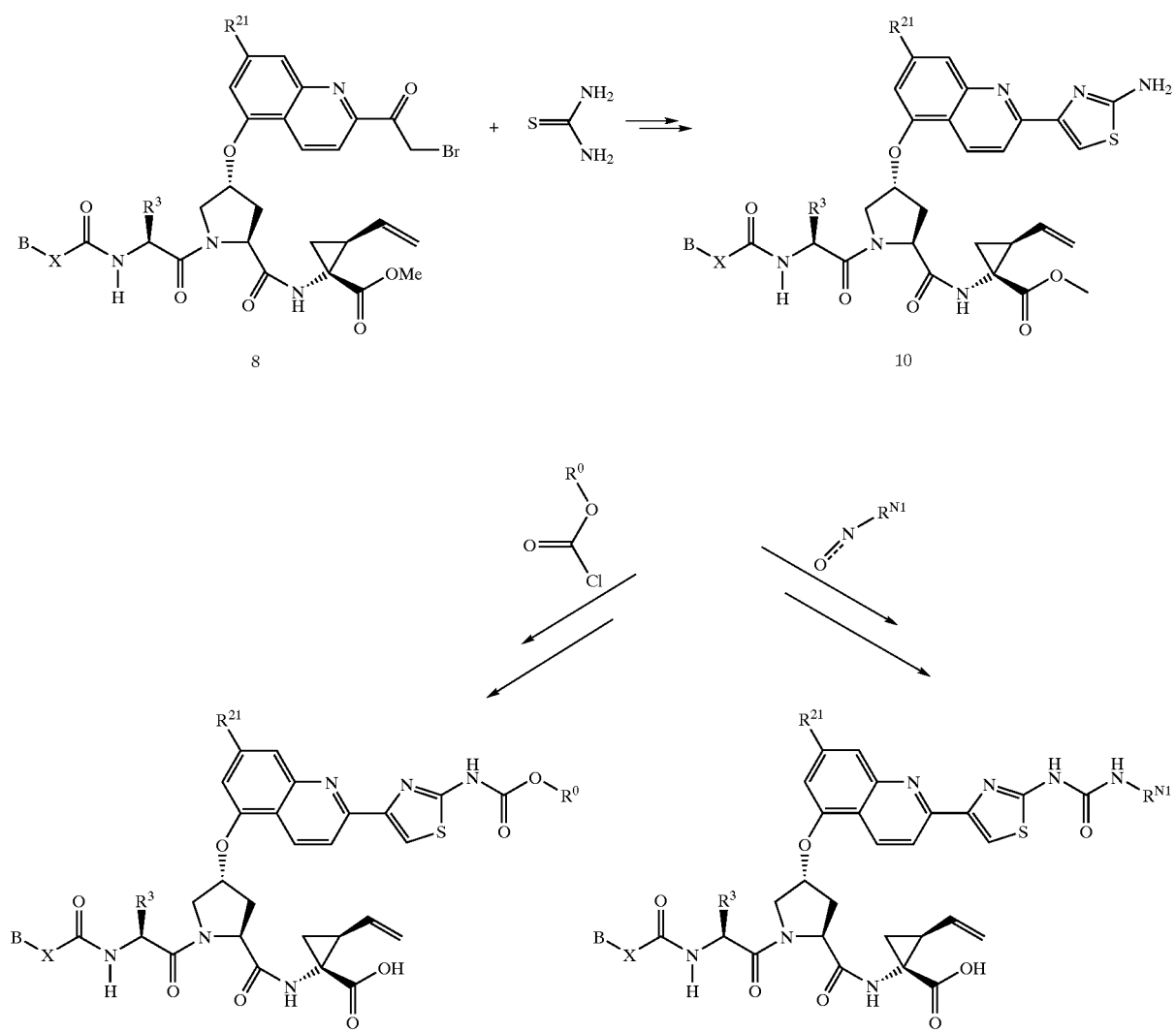

Alternatively the compounds can be synthesized starting with a preformed dipeptide bromoketone such as 12 in scheme IV. This bromoketone can be converted to the required aminothiazole derivatives by reaction with thioureas 9 followed by incorporation of the carbamate or urea P3 group using standard coupling conditions as described above.

Scheme IV:
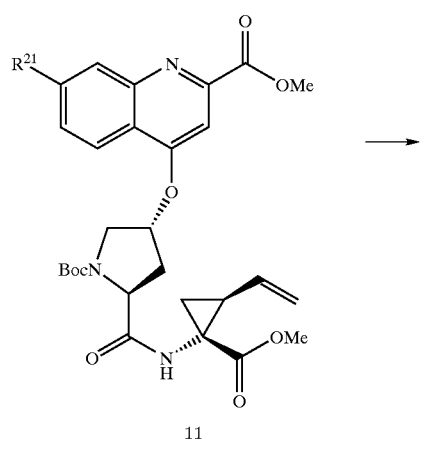
11
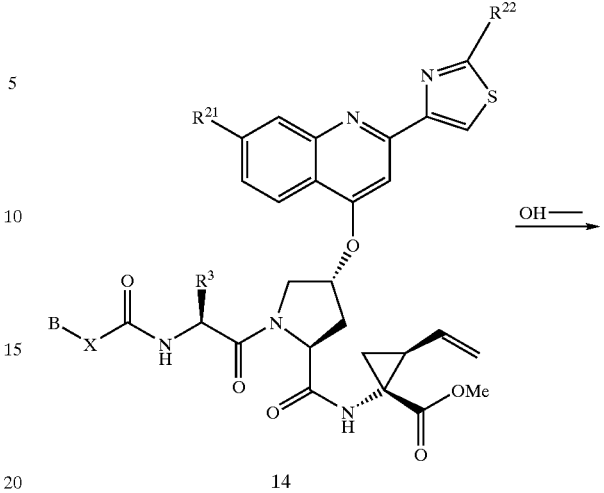
14
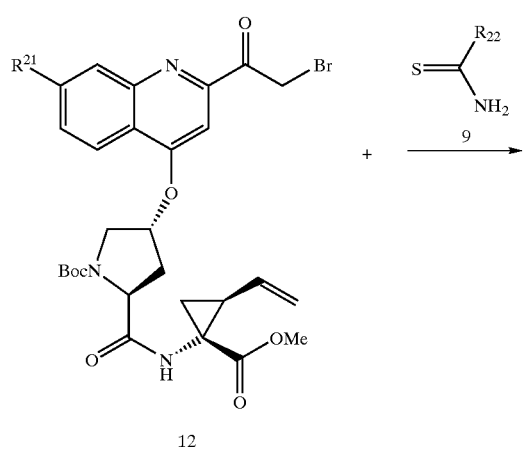
12
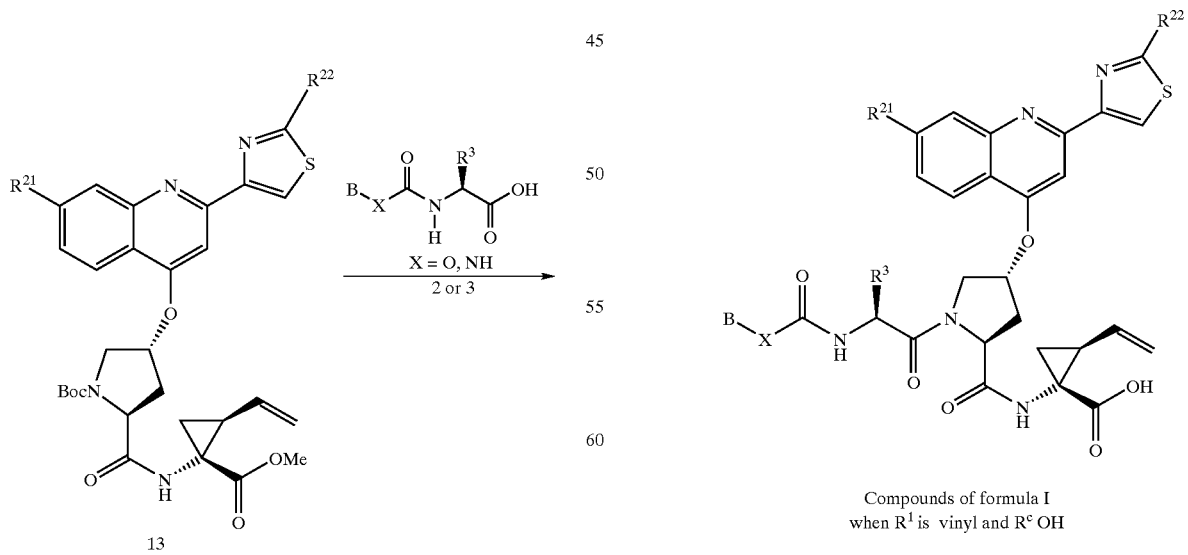
13
Compounds of formula I
when R¹ is vinyl and Rᶜ OH The method described in Scheme IV can also be used for the synthesis of the claimed compounds by making a permutation library.

Compounds of formula I wherein $R^c$ is $NHSO_2R^S$ as defined herein are prepared by coupling the corresponding acid of formula I (i.e. $R^c$ is hydroxy) with an appropriate sulfonamide of formula $R^s\ SO_2NH_2$ in the presence of a coupling agent under standard conditions. Although several commonly used coupling agents can be employed, TBTU and HATU have been found to be practical. The sulfonamides are available commercially or can be prepared by known methods.

EXAMPLES

The present invention is illustrated in further detail by the following non-limiting examples. Other specific ways of synthesis or resolution can be found in WO 00/59929, WO 00/09558 and WO 00/09543.

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Flash chromatography was carried out on silica gel ($SiO_2$) according to Still's flash chromatography technique (W. C. Still et al., J. Org. Chem., (1978), 43, 2923).

Abbreviations used in the examples include:

DBU: 1,8-diazabicyclo[5.4.0]undec-7-ene; DCM: dichloromethane; DIAD: diisopropylazodicarboxylate; DIEA: diisopropylethylamine; DIPEA: diisopropylethyl amine; DMF: N,N-dimethylformamide; DMAP: 4-(dimethylamino) pyridine; EtOAc: ethyl acetate; HATU: [O-7-azabenzotriazol-1-yl)-1,1,3,3-tetramethyluronium hexafluorophosphate]; HPLC: high performance liquid chromatography; MS: mass spectrometry (MALDI-TOF: Matrix Assisted Laser Desorption Ionization-Time of Flight, FAB: Fast Atom Bombardment); Me: methyl; MeOH: methanol; Ph: phenyl; R.T.: room temperature (18 to 22°); tert-butyl or t-butyl: 1,1-dimethylethyl; Tbg: tert-butyl glycine: tert-leucine; TBTU: 2-(1H-benzotriazole-1-yl)-1,1,3,3-tetramethyl uronium tetrafluoroborate; TFA: trifluoroacetic acid; and THF: tetrahydrofuran.

P1 Building Blocks

P1 moieties of compounds of Formula (I) were prepared using the protocols outlined in WO 00/59929, published Oct. 12, 2000, and WO 00/09543, published on Feb. 24, 2000. In particular, reference is made to pages 33–35, Example 1 of WO00/59929 and Pages 56–69, Example 9–20 of WO00/09543 for the preparation of 1-aminocyclopropanecarboxylic acid P1 moieties.

P2 Building Blocks

P2 moieties of compounds of Formula (I) were prepared using the protocols outlined in WO00/59929, published Oct. 12, 2000, and WO00/09543, published on Feb. 24, 2000.

Example 1

Synthesis of 2-carbomethoxy-7-dimethylamino-4-hydroxyquinoline (6b):

Step 1:

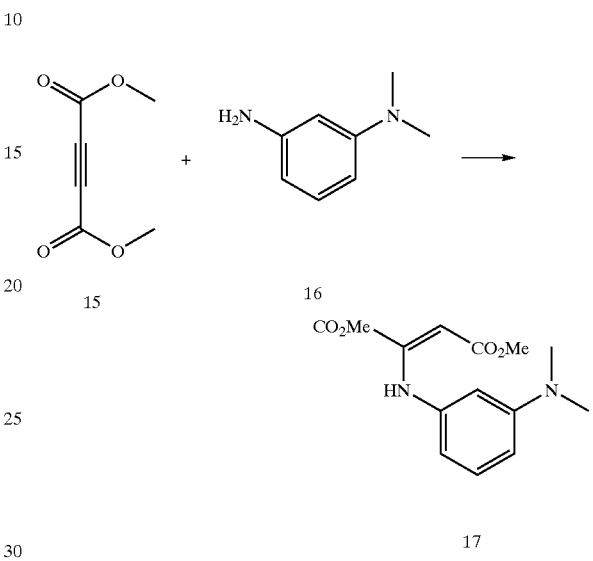

Commercially available N,N-dimethyl-1,3-phenylene diamine dihydrochloride salt (12 g) was neutralized with solid $NaHCO_3$ (partitioned between $H_2O$ and EtOAc). After neutralization, the phases were separated and the organic phase dried and concentrated to give a brownish oil (7.8 g, 57.3 mmol) which was used as is in the next step. Dimethyl acetylene dicarboxylate 15 (7.044 mL, 57.3 mmol) was dissolved in MeOH and treated with the neutralized aniline 16 (portionwise) in MeOH at 0° C. Considerable heat was generated (exothermic reaction). The mixture (brown) was heated at 65° C. for 2 hours. The brown solution was concentrated to dryness, extracted into EtOAc and washed with sat. $NaHCO_3$ (aq), followed by brine, dried ($MgSO_4$), filtered, and concentrated. The crude mixture was purified by flash chromatography using a 10% EtOAc/hexane solvent to afford 12 g of compound 17.

MS: electrospray: $(M+H)^+$; 279 and $(M-H)^-$; 277.

Step 2:

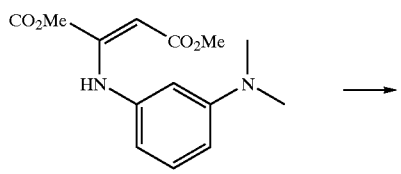

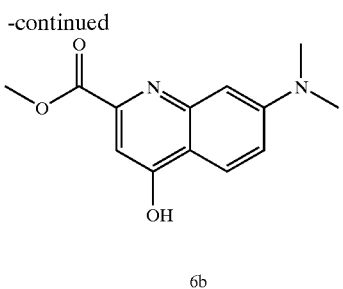

6b

The diester precursor 17 (6 gm, 21.56 mmol) was dissolved in diphenyl ether (10 mL) which was preheated to 245° C. in a sand bath. The mixture was heated a further 7 minutes (addition lowers the temperature to about 230° C.). The final internal temperature was 245° C. The darkened solution was removed from the sand bath and air cooled for a few minutes and then further cooled by an ice bath. The product precipitated out after a few minutes. The solution was left a few hours to allow the product to completely precipitate and then was filtered to give a yellow solid. The same protocol was duplicated with the remaining half of the diester precursor (6 g) to give a yellow solid. The solids (identical) were combined and suspended in $Et_2O$ before being filtered. The yellow solid was washed several times with diethyl ether and then with hexane to give 6.25 g of the title compound 6b (59%).

Reverse Phase HPLC: (homogeneity=96%). Mass Spectrum: electrospray, (M+Na)$^+$; 269, (M-H)$^-$; 244.9.

Example 2
Preparation of 3-thioallophanic acid isopropyl ester (9a)

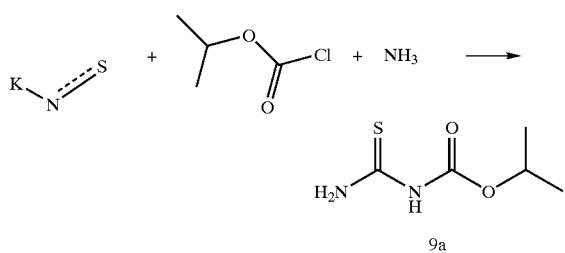

9a

Potassium thiocyanate (4.8 g, 0.049 mol) was dissolved in water (10 mL) and acetonitrile (30 mL) before being treated with pyridine (0.25 mL, 3.09 mmol, 6.3 mol %). The solution was cooled to 0° C. (ice bath) and then treated dropwise with isopropylchloroformate in toluene (51 mL, 0.051 mol, 1.05 eq.) over 2 hours. The mixture was stirred rapidly to ensure mixing of the layers to give an orange solution. The mixture was allowed to stir overnight and then cooled to 0° C. before being treated with 10% HCl (aq) (2 mL) to dissolve the salts. This mixture was then treated with ammonia in dioxane (0.5M solution, 110 mL, 1.12 eq.) from a dropping funnel over 2 h. The mixture was allowed to warm to RT and stirred overnight. The mixture was quenched with water (100 mL) and the phases separated. The aqueous phase was re-extracted with EtOAc and the combined organic phase dried over $MgSO_4$, filtered and concentrated to give a yellow solid. This was dissolved in a minimum amount of EtOAc (ca. 15 mL) and then precipitated with hexane (ca. 100 mL) to give a yellow precipitate. This material was filtered and then washed with hexane to give the desired urea as a yellow solid (3.7 g, 47%).

$^1$H NMR (400 MHz, DMSO-d$_6$) δ 10.76 (s, 1H), 9.22 (s, 1H), 9.00 (s, 1H), 4.91–4.82 (m, 1H), 1.22 (d, J=7.3 Hz, 6H).

Example 3
Preparation of 3-thioallophanic acid cyclopentyl ester (9b)

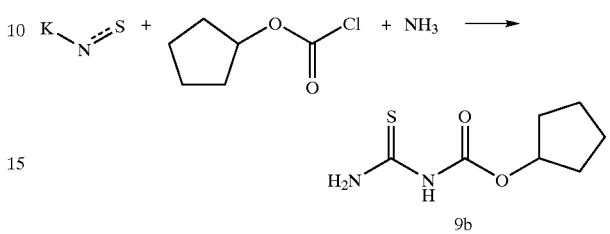

9b

Using the procedure described above but using cyclopentylchloroformate instead of isopropylchloroformate gave the desired compound (9b).

P3 Building Blocks

P3 moieties of compounds of Formula (I) were generally prepared using the protocols outlined in WO00/59929, published Oct. 12, 2000, and WO00/09543, published on Feb. 24, 2000.

Example 4
Preparation of Carbamate 2a

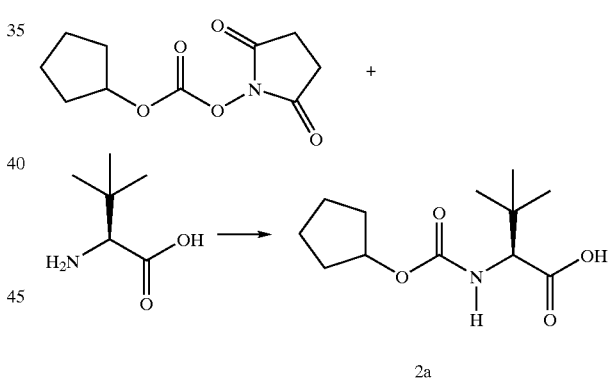

2a

THF (350 mL) was added to a flask containing carbonic acid cyclopentyl ester 2,5-dioxo-pyrrolidin-1-yl ester (9.00 g; 39.6 mmol) and tert-butyl glycine (6.24 g; 47.5 mmol) resulting in a suspension. Distilled water (100 mL) was added with vigorous stirring. A small amount of solid remained undissolved. Triethylamine (16.6 mL; 119 mmol) was then added resulting in a homogenous solution which was stirred at R.T. After 2.5 h, the THF was evaporated and the aqueous residue diluted with water (100 mL). The reaction was rendered basic by the addition of 1 N NaOH (25 mL–final pH >10). The solution was washed with EtOAc (2×200 mL) and the aqueous phase acidified with 1 N HCl (ca. 70 mL–final pH <2). The turbid solution was extracted with EtOAc (200+150 mL). The extract was dried (MgSO$_4$) and evaporated to give carbamate 2a as a white solid (8.68 g).

Preparation of Other Carbamates

Using the procedure described above and using appropriate combinations of tert-butyl glycine, cyclopentyl glycine, or cyclohexyl glycine and carbonic acid cyclobutyl, cyclopentyl, or cyclohexyl ester 2,5-dioxo-pyrrolidin-1-yl ester, carbamates of the following formulas were prepared:

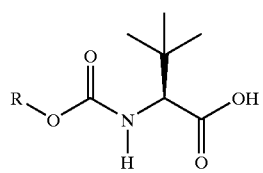

R =

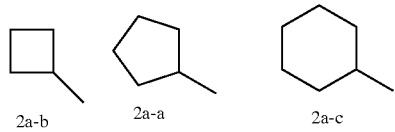

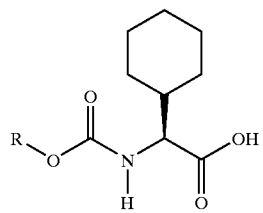

R =

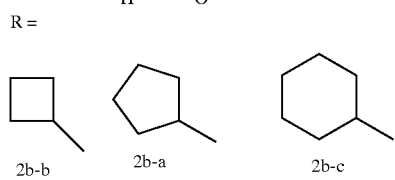

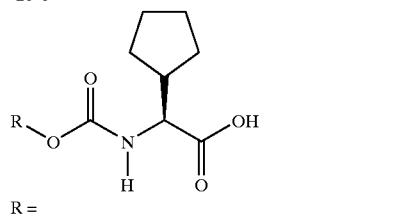

R =

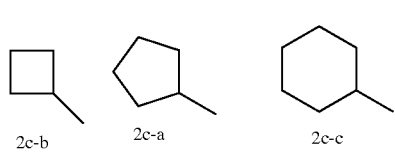

Example 5

Preparation of Urea 3a

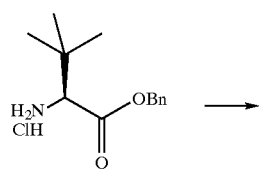

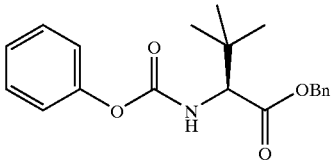

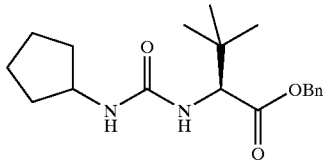

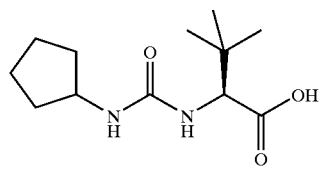

3a

A solution of tert-butyl glycine benzyl ester hydrochloride salt (2.55 g; 9.89 mmol) in THF (20 mL) and pyridine (2.0 mL; 24.73 mmol) was cooled to 0° C. Phenyl chloroformate (1.30 mL; 10.19 mmol) was added dropwise to the cooled solution. The resulting suspension was stirred for 5 min at 0° C., then at R.T. for 1.5 h. The reaction mixture was diluted with EtOAc, washed with 10% citric acid (2×) water (2×) saturated $NaHCO_3$ (2×), water (2×) and brine (1×), dried ($MgSO_4$), filtered and evaporated to obtain the crude compound as a nearly colorless oil (3.73 g; >100%; assume 9.89 mmol). The crude product (1.01 g; 2.97 mmol) was dissolved in DMSO (6.5 mL) and cyclopentylamine was added dropwise. The reaction mixture was stirred at R.T. for 45 min. The reaction mixture was diluted with EtOAc. The organic phase was washed with 10% citric acid (2×), water (2×), saturated $NaHCO_3$ (2×), water (2×) and brine (1×), dried ($MgSO_4$), filtered and evaporated to give the crude cyclopentyl urea-Tbg-OBn product as a nearly colorless oil. The crude material was purified by flash column chromatography with silica using hexane:EtOAc 9:1 to remove the less polar impurities and 7:3 to elute the purified product as a thick colorless oil (936 mg; 95%). The benzyl ester product (936 mg; 2.82 mmol) was deprotected under a hydrogen filled balloon at R.T. in absolute ethanol (15 mL) solution by stirring the solution with 10% Pd/C (93.6 mg) for 5.5 h. The reaction mixture was filtered through a 0.45 micron filter and evaporated to dryness to provide urea 3a as a white solid (668.8 mg; 98%)

$^1$H NMR (400 MHz,DMSO-$d_6$): δ 12.39 (s, 1H), 6.09 (d, J=7.4 Hz, 1H), 5.93 (d, J=9.4 Hz, 1H), 3.90 (d, J=9.4 Hz, 1H), 3.87–3.77 (m, 1H), 1.84–1.72 (m, 2H), 1.63–1.42(m, 4H), 1.30–1.19 (m, 2H), 0.89 (s, 9H). M.S.(electrospray): 241.0 (M−H)$^-$ 243.0 (M+H)$^+$. Reverse Phase HPLC Homogeneity (0.06% TFA; $CH_3CN$: $H_2O$): 99%.

Tripeptide Analogs

Example 6
Preparation of Compound 105

Step 1: Synthesis of tripeptide 7a:

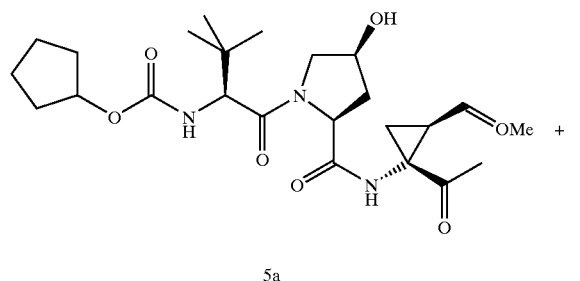

5a

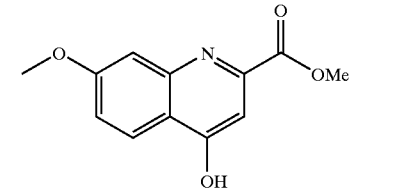

6a

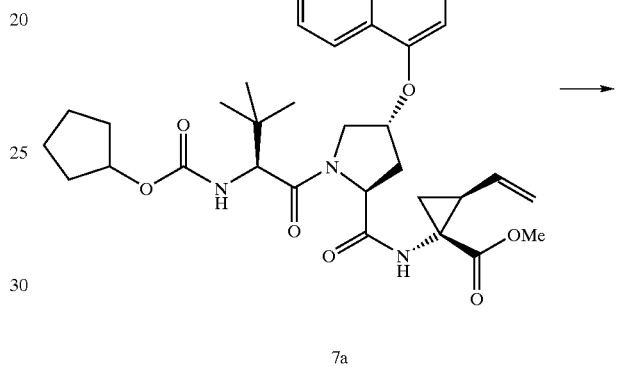

7a

To tripeptide 5a (1.0 g; 2.09 mmol) dissolved in THF (35 mL), hydroxyquinoline 6a (729 mg; 3.13 mmol) and triphenylphosphine (1.1 g; 4.2 mmol) were added. The yellow suspension was cooled in an ice bath and DIAD (821 μL, 4.2 mmol) was added dropwise. The solution was stirred at ice bath temperature for 30 min, and at R.T. for 16 h. The solution was evaporated to dryness and the residue was dissolved in EtOAc, washed with a saturated sodium bicarbonate solution (2×), water (2×) and brine (1×), dried (MgSO₄), filtered and evaporated to obtain a yellow oil which precipitated on standing. The crude solid was suspended in DCM and the insoluble material was filtered off. The solution was concentrated and the residue purified by flash chromatography in hexane: EtOAc; 5:5 to remove all less polar impurities and in CHCl₃:EtOAc; 80:20 until all the Ph₃P=O has eluted. The desired compound was eluted with CHCl₃:EtOAc; 65:35 as a white solid (1 g; 70% yield).

M.S.(electrospray): 693.3 (M−H)⁻ 695.4 (M+H)⁺ 717.4 (M+Na)⁺. Reverse Phase HPLC Homogeneity (0.06% TFA; CH₃CN:H₂O): 99%.

Step 2: Selective monohydrolysis of ester 7a:

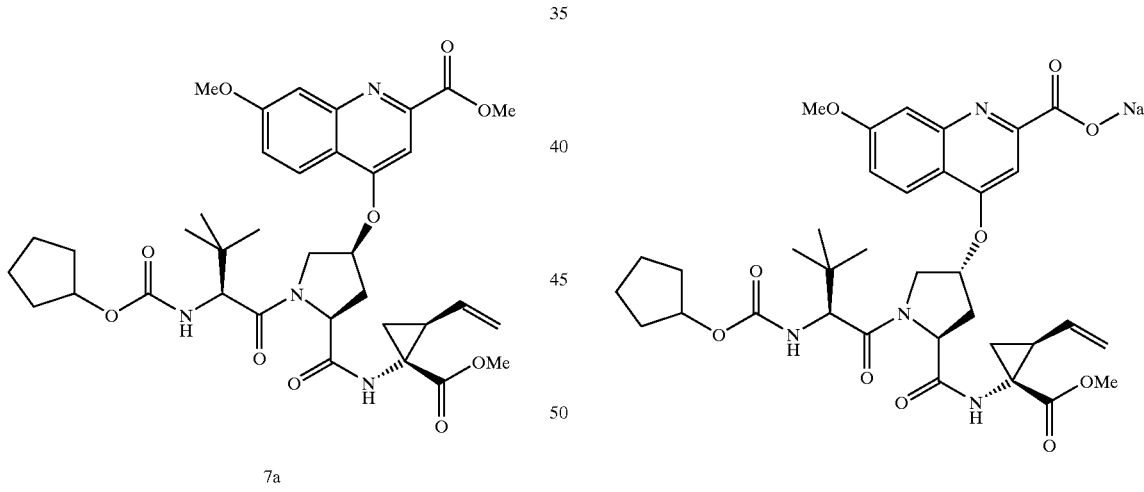

7a

18

Tripeptide 7a (1 g; 1.44 mmol) was dissolved in THF (10 mL), MeOH (5 mL), water (5 mL) and a 1N aqueous solution of NaOH (1.5 mL) were added and the solution was stirred at R.T. for 2 h. The mixture was evaporated to dryness and then co-evaporated with MeOH:toluene (1:1; 4×), toluene (2×) and diethyl ether (2×) to obtain salt 18 (water-free) as a white flaky solid (1.04 g; 100% yield)

M.S.(electrospray): 679.3 (M−H)⁻ 681.3 (M+H)⁺ 703.3 (M+Na)⁺. Reverse Phase HPLC Homogeneity (0.06% TFA; CH₃CN:H₂O): 95%.

Step 3: Synthesis of diazoketone 19:

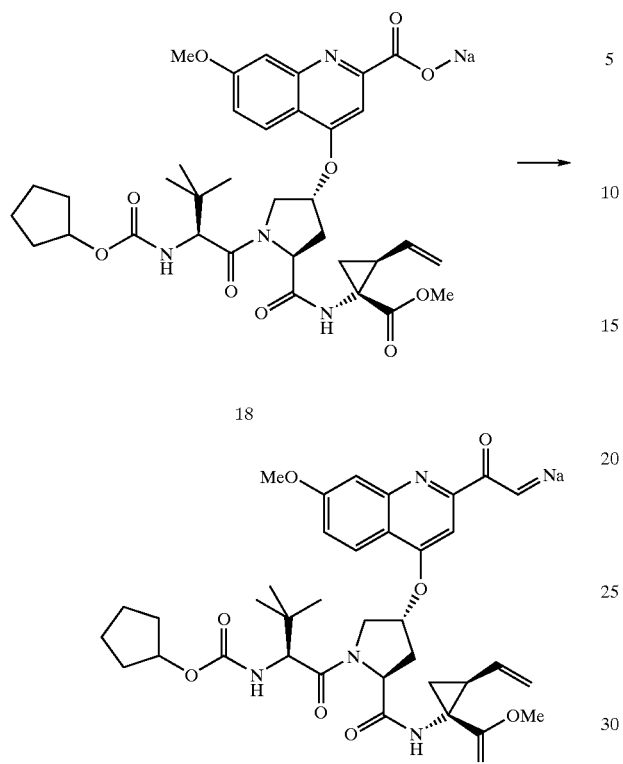

18

Sodium salt 18 (assume 1.44 mmol) was dissolved in THF (16 mL), triethylamine (301 μL; 2.16 mmol) was added and the solution cooled to 0° C. Isobutylchloroformate (280 μL; 2.16 mmol) was added dropwise and the white suspension was stirred at 0° C. for 75 min, followed by the addition of a solution of diazomethane (0.67M in diethyl ether; 13 mL; 8.64 mmol). The reaction mixture is stirred 1 h at 0° C., 45 min at R.T. and evaporated to provide a thick suspension. This suspension was dissolved in EtOAc and water. The organic solution was washed with saturated $NaHCO_3$ (2×), water (2×) and brine (1×), dried ($MgSO_4$), filtered and evaporated to give the diazoketone 19 as an ivory solid (crude material used for next step; assume 1.44 mmol). M.S.(electrospray): 703.3 (M–H)⁻ 705.3 (M+H)⁺. Reverse Phase HPLC Homogeneity (0.06% TFA; $CH_3CN$: $H_2O$): 91%.

Step 4: Synthesis of bromoketone 8a:

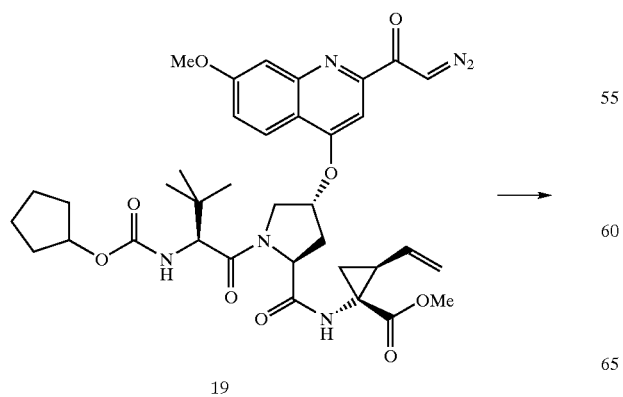

19

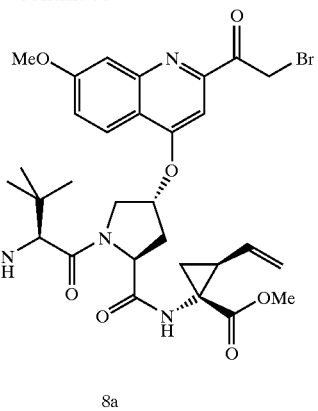

8a

At 0° C., to a solution of diazoketone 19 (1.44 mmol) in THF (24 mL) was added dropwise an HBr solution (1.0 mL) and the mixture was stirred for 1 h. The solution was diluted with EtOAc, washed with a saturated $NaHCO_3$ solution (2×), water (2×) and brine (1×), dry ($MgSO_4$), filtered and evaporated to give the desired bromoketone 8a as an ivory-beige solid (1.1 g; assume 1.44 mmol). M.S.(electrospray): 757.3 (M) 759.3 (M+2)

Step 5: Preparation of aminothiazolyl derivative 10a:

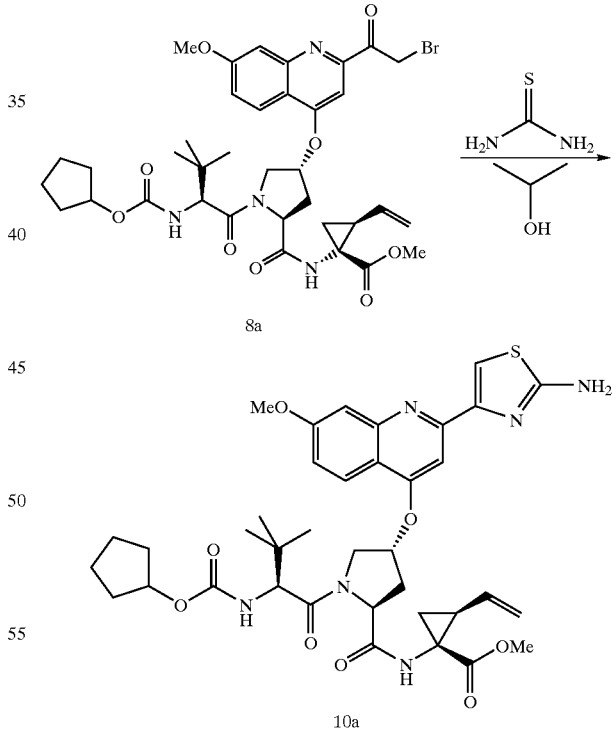

10a

α-Bromoketone 8a (0.82 g; 1.08 mmol) was combined with commercially available thiourea (167 mg; 2.19 mmol) in isopropanol (20 mL) and the yellow solution was heated at 75° C. for 1 hour. The solution was cooled to R.T. and evaporated to dryness. The residue was dissolved in EtOAc. The EtOAc solution was washed with saturated $NaHCO_3$ (2×), water (1×) and brine (1×), dried ($MgSO_4$), and evaporated to give the crude product 10a as a yellow solid (0.78 g, 1.06 mmol, 98%).

M.S.(electrospray): 733.2 (M−H)⁻ 735.2 (M+H)⁺. Reverse Phase HPLC Homogeneity (0.06% TFA; $CH_3CN:H_2O$): 93%.

Step 6: Preparation of intermediate 20

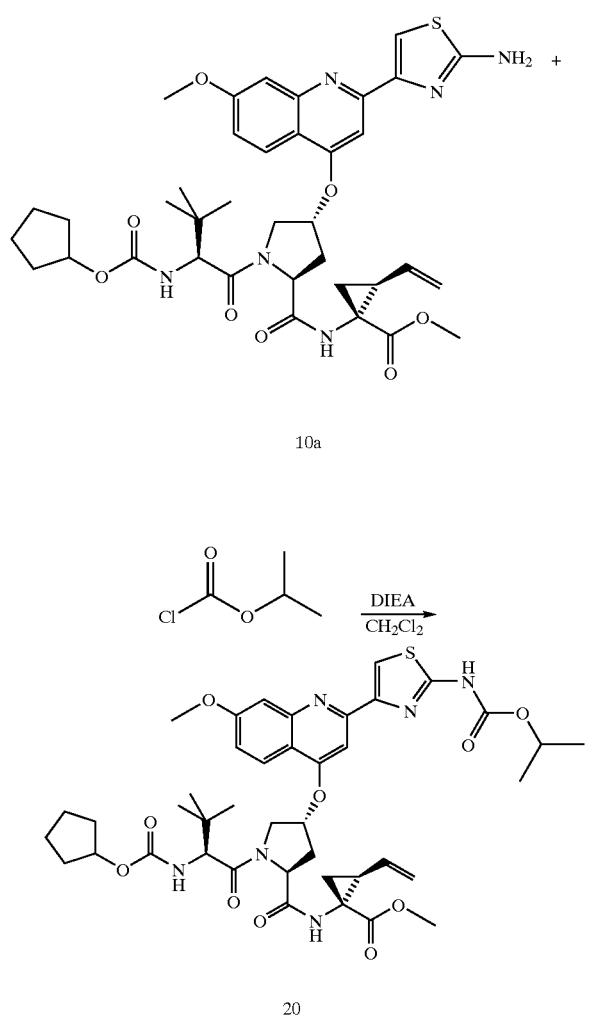

To a solution of the thiazolyl amine 10a (55 mg; 0.075 mmol) in dichloromethane (3.0 mL) was added DIEA (70 μL; 0.402 mmol) followed by 1M isopropyl chloroformate/ toluene (950 μL; 0.947 mmol). The mixture was placed in a preheated oil bath (40° C.) and stirred overnight. The reaction was found to be incomplete by analytical HPLC and additional reagent was added (DIEA: 35 μL; 0.201 mmol and 380 μL; 0.379 mmol), stirred at an oil bath temperature of 40° C. for 7 hours and overnight at room temperature. The reaction was concentrated, diluted with EtOAc, washed with water, saturated sodium bicarbonate and brine, dried ($MgSO_4$), filtered and evaporated to dryness to obtain the crude product 20 (60 mg; 0.073 mmol; 98% yield).

Step 7: Final hydrolysis to compound 105

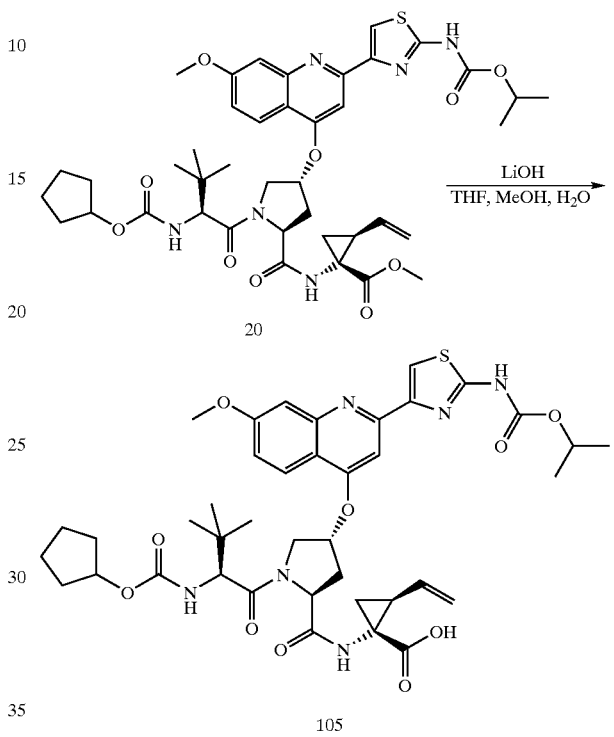

A solution of methyl ester 20 (60 mg; 0.073 mmol) in THF (2.5 mL), MeOH (0.5 mL) and an aqueous solution of LiOH (37 mg; 0.881 mmol) in water (1 mL) was stirred overnight. The organic solution is concentrated to provide an off white suspension. The crude material was purified by preparatory HPLC (YMC Combiscreen ODS-AQ, 50×20 mm ID S-5 micron, 120 A; λ=220 nm) using a linear gradient and 0.06% TFA $CH_3CN/H_2O$. The pure fractions were combined, concentrated and lyophilized to provide compound 105 (from Table 1) as the TF salt (27 mg; 46% yield).

$^1$H NMR (400 MHz,DMSO-$d_6$): ca, 9:1 mixture of rotamers, major isomer description; δ12.02 (br s, 1H), 8.59 (s, 1H), 8.49–8.26 (m, 1H), 8.18 (d, J=9.0 Hz, 1H), 7.70–7.48 (m, 2H), 7.25–7.15 (m, 1H), 7.07 (d, J=8.2 Hz, 1H), 5.77–5.65 (m, 1H), 5.63–5.53 (m, 1H), 5.23–5.15 (m, 1H), 5.10–4.95 (m, 2H), 4.60–4.50 (m, 1H), 4.49–4.38 (m, 2H), 4.09–4.02 (m, 1H), 3.98–3.88 (m, 1H), 3.95 (s, 3H), 2.62–2.52 (m, 1H), 2.34–2.23 (m, 1H), 2.05–1.96 (m, 1H), 1.70–1.38 (m, 7H), 1.31 (d, J=6.3 Hz, 6H), 1.31–1.01 (m, 3H), 0.96 (s, 9H). M.S.(electrospray): 805.3 (M−H)⁻ 807.3 (M+H)⁺. Reverse Phase HPLC Homogeneity (0.06% TFA; $CH_3CN:H_2O$): 99%

Example 7
Synthesis of Compound 102

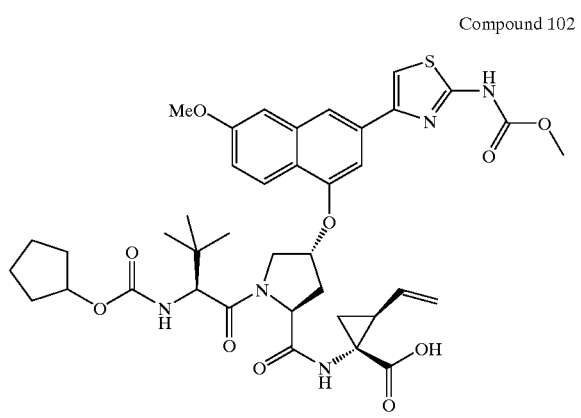

Compound 102

Compound 102 is prepared using the same procedure as the one described in example 6 but using methyl chloroformate instead of isopropyl chloroformate in step 6.

$^1$H NMR (400 MHz, DMSO-$d_6$): ca, 9:1 mixture of rotamers, major isomer description; δ 8.56 (s, 1H), 8.47–8.20 (m, 1H), 8.20–8.12 (m, 1H), 7.67–7.45 (m, 2H), 7.24–7.14 (m, 1H), 7.01 (d, J=8.3 Hz, 1H), 5.78–5.66 (m, 1H), 5.62–5.51 (m, 1H), 5.23–5.16 (m, 1H), 5.09–5.03 (m, 1H), 4.64–4.54 (m, 1H), 4.50–4.39 (m, 2H), 4.07 (d, J=8.6 Hz, 1H), 3.99–3.92 (m, 1H), 3.95 (s, 3H), 3.80 (s, 3H), 2.63–2.53 (m, 1H), 2.34–2.24 (m, 1H), 2.06–1.97 (m, 1H), 1.77–1.22 (m, 10H), 0.97 (s, 9H). M.S.(electrospray): 777.2 (M−H)$^−$ 779.2 (M+H)$^+$. Reverse Phase HPLC Homogeneity (0.06% TFA; CH$_3$CN:H$_2$O): 99%

Example 8
Synthesis of Compound 101

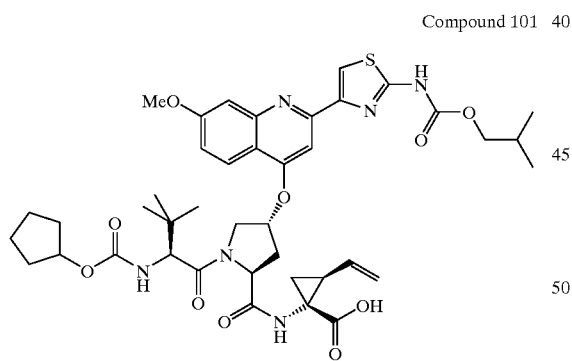

Compound 101

Compound 101 is prepared using the same procedure as the one described in example 6 but using isobutyl chloroformate instead of isopropyl chloroformate in step 6.

$^1$H NMR (400 MHz, DMSO-$d_6$): ca, 9:1 mixture of rotamers, major isomer description; δ 8.57 (s, 1H), 8.42–8.31 (m, 1H), 8.17 (d, J=9.2 Hz, 1H), 7.66–7.52 (m, 2H), 7.25–7.16 (m, 1H), 7.01 (d, J=8.3 Hz, 1H), 5.78–5.66 (m, 1H), 5.62–5.55 (m, 1H), 5.23–5.16 (m, 1H), 5.09–5.03 (m, 1H), 4.61–4.53 (m, 1H), 4.50–4.40 (m, 2H), 4.06 (d, J=8.6, 1H), 4.03 (d, J=5.4 Hz, 2H), 3.99–3.92 (m, 1H), 3.95 (s, 3H), 2.62–2.53 (m, 1H), 2.34–2.25 (m, 1H), 2.05–1.93 (m, 2H), 1.69–1.22 (m, 10H), 0.97 (s, 9H), 0.95 (d, J=6.7 Hz, 6H). M.S.(electrospray):819.5 (M−H)$^−$ 821.4 (M+H)$^+$. Reverse Phase HPLC Homogeneity (0.06% TFA; CH$_3$CN:H$_2$O): 98%

Example 9
Synthesis of Compound 103

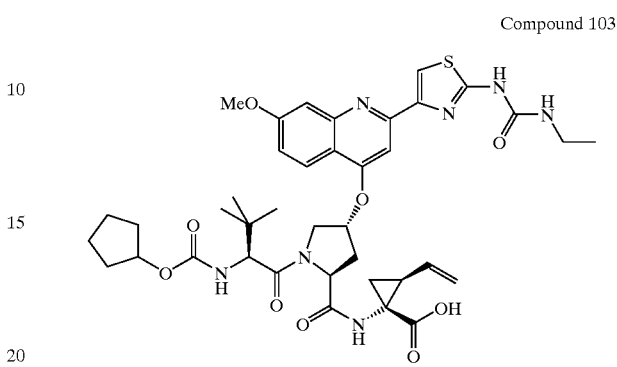

Compound 103

The synthesis starts with aminothiazole derivative 10a described in step 6 of example 6.

Step 1:

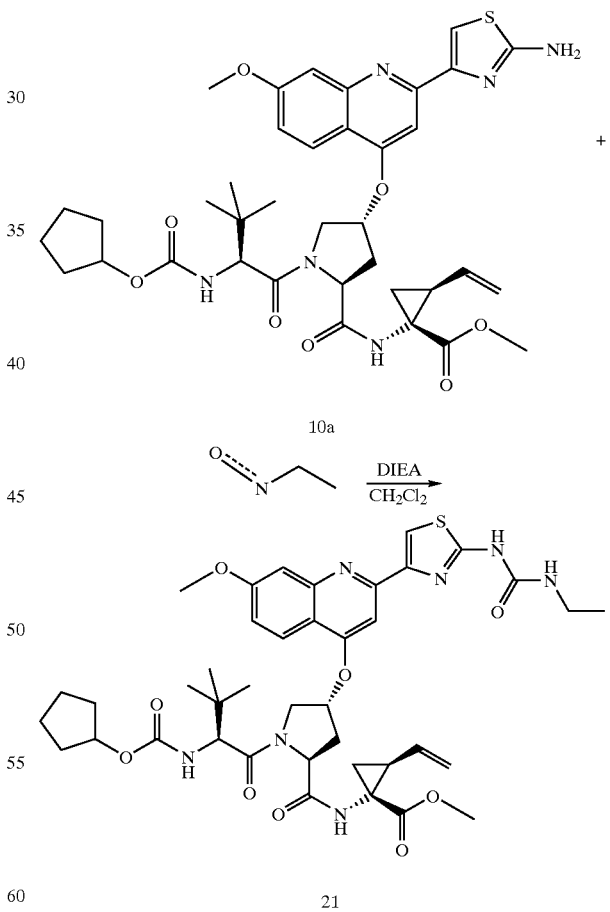

To a solution of the thiazolylamine derivative 10a (50 mg; 0.068 mmol) in dichloromethane (2.0 mL) was added commercially available ethylisocyanate (17 μL; 0.215 mmol) followed by DIEA (36 μL; 0.207 mmol). The reaction was stirred overnight and found to be incomplete by analytical HPLC. Additional reagent was added (ethylisocyanate: 2×17 μL; 0.430 mmol) but the reaction went to completion only after being placed in a preheated oil bath (40° C.) for 3 hours. The reaction was concentrated, diluted with EtOAc, washed with saturated sodium bicarbonate and brine, dried (MgSO$_4$), filtered and evaporated to dryness to obtain the methyl ester 21 (59 mg; >0.068 mmol; >100% yield).

Step 2: Hydrolysis of methyl ester 21

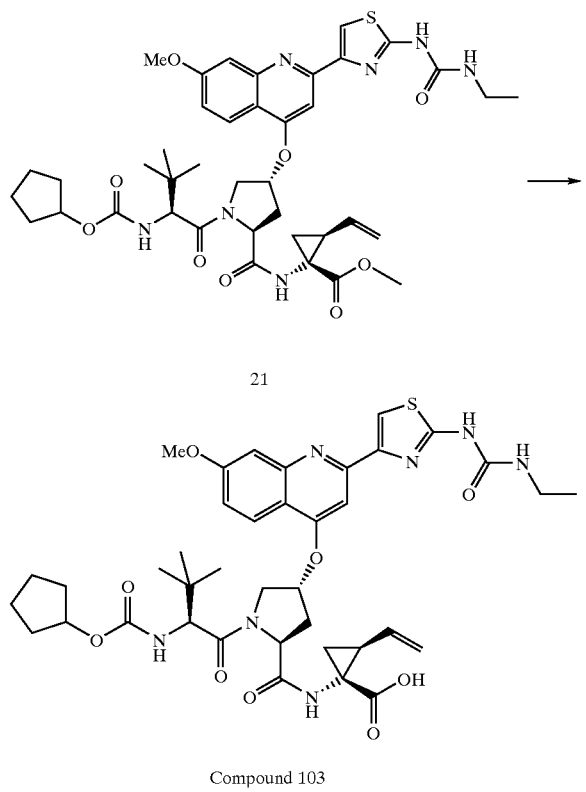

21

Compound 103

To a solution of methyl ester 21 (0.068 mmol) in a 3 mL mixture of THF:H$_2$O (2.5:1), was added a 1N solution of NaOH (0.55 mL, 0.55 mmol). 0.5 mL of MeOH was required to obtain an homogeneous solution. The resulting reaction was stirred at room temperature for 4 hours. The organic solution was concentrated to provide an off white suspension. The crude material was purified by preparatory HPLC (YMC Combiscreen ODS-AQ, 50×20 mm ID S-5 micron, 120 A; λ=220 nm) using a linear gradient and 0.06% TFA CH$_3$CN/H$_2$O. The pure fractions were combined, concentrated and lyophilized to provide the product 103 as the TF salt (34 mg; 55% yield).

$^1$H NMR (400 MHz,DMSO-d$_6$): ca, 9:1 mixture of rotamers, major isomer description; δ 10.65 (s, 1H), 8.57 (s, 1H), 8.40–8.20 (m, 1H), 8.18 (d, J=9.2 Hz, 1H), 7.72–7.54 (m, 2H), 7.27–7.18 (m, 1H), 7.01 (d, J=8.0 Hz, 1H), 6.82–6.68 (m, 1H), 5.78–5.66 (m, 1H), 5.66–5.59 (m, 1H), 5.23–5.16 (m, 1H), 5.09–5.03 (m, 1H), 4.59–4.41 (m, 3H), 4.06 (d, J=8.2, 1H), 3.99–3.91 (m, 1H), 3.95 (s, 3H), 3.25–3.15 (m, 2H), 2.63–2.54 (m, 1H), 2.36–2.26 (m, 1H), 2.07–1.98 (m, 1H), 1.70–1.23 (m, 10H), 1.10 (t, J=7.0 Hz, 3H), 0.97 (s, 9H). M.S.(electrospray): 790.2 (M–H)$^-$ 792.3 (M+H)$^+$. Reverse Phase HPLC Homogeneity (0.06% TFA; CH$_3$CN:H$_2$O): 99%

Dipeptide Analogs

Example 10

Synthesis of Bromoketone 12a:

Step 1: Monohydrolysis of diester 11a:

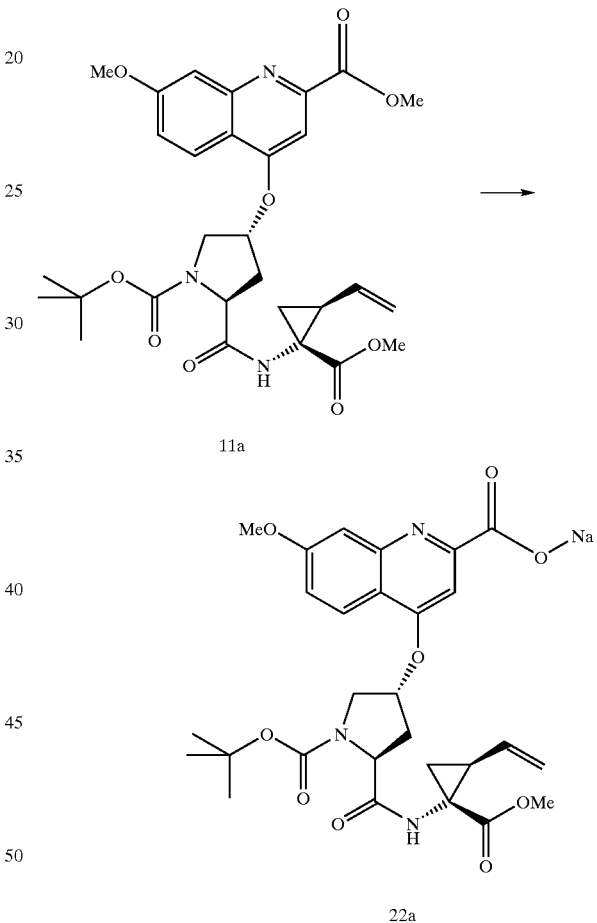

11a

22a

Dipeptide 11a (4.0 g; 7.02 mmol) was dissolved in THF (20 mL) and MeOH (10 mL), water (10 mL) and a 1N NaOH aqueous solution (1.05 equivalents; 7.4 mL) was added. The solution stirred at R.T. for 2 h 45 min. The mixture was evaporated to dryness. The residue was diluted with water, frozen and lyophilized to provide sodium salt 22a as a white amorphous solid (4.28 g).

M.S.(electrospray): 554.2 (M–H)$^-$ 556.3 (M+H)$^+$ 578.2 (M+Na)$^+$. Reverse Phase HPLC Homogeneity (0.06% TFA; CH$_3$CN:H$_2$O): 96%.

Step 2: Synthesis of Dipeptide Diazoketone 23a:

Step 2: synthesis of dipeptide diazoketone 23a:

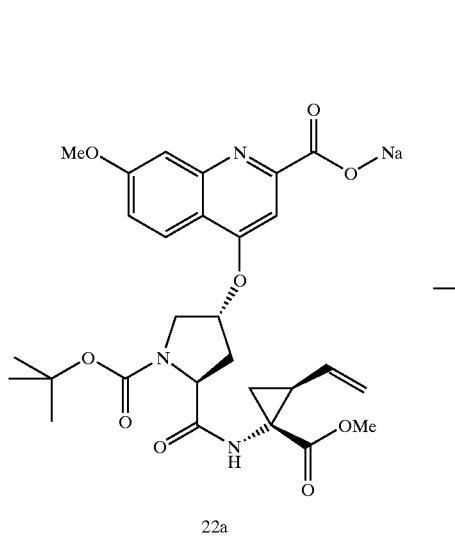

22a

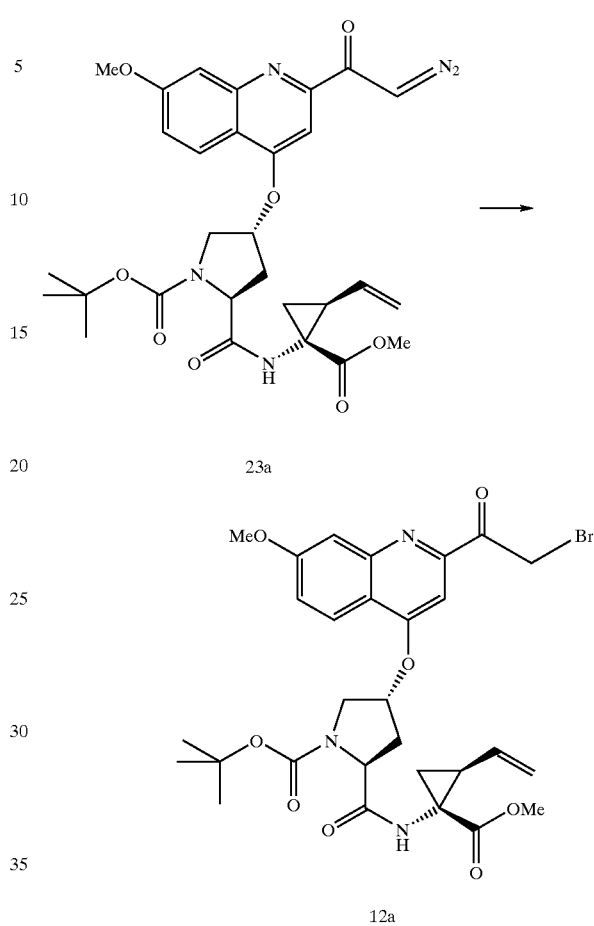

Step 3: synthesis of dipeptide bromoketone 12a

23a

Sodium salt 22a (assume 7.02 mmol) was dissolved in THF (78 mL); triethylamine (1.37 mL; 9.83 mmol) was added and the solution cooled to 0° C. Isobutylchloroformate (1.28 mL; 9.83 mmol) was added dropwise and the white suspension was stirred at 0° C. for 2 h, followed by the addition of a solution of diazomethane (0.67M in diethyl ether; 63 mL; 42.13 mmol). The reaction mixture was stirred 1 h at 0° C., 1.25 h at R.T. and evaporated to provide a thick suspension. This suspension was dissolved in EtOAc and water. The organic solution was washed with saturated NaHCO₃ (2×), water (2×) and brine (1×), dried (MgSO₄), filtered and evaporated to give the diazoketone 23a as an beige solid (crude material used for next step; assume 7.02 mmol).

M.S.(electrospray): 578.2 (M−H)⁻ 580.3 (M+H)⁺. Reverse Phase HPLC Homogeneity (0.06% TFA; CH₃CN:H₂O): 90%.

At 0° C., to a solution of diazoketone 23a (assume 1.44 mmol) in THF (116 mL) was added dropwise a 48% aqueous HBr solution (5.1 mL) and the mixture was stirred for 2 h. The solution was diluted with EtOAc, washed with a saturated NaHCO₃ solution (2×), water (2×) and brine (1×), dry (MgSO₄), filtered and evaporated to give the desired bromoketone 12a as a beige solid (4.25 g; 6.72 mmol).

M.S.(electrospray): 632 (M) 634.2 (M+2)

Example 11
Synthesis of Bromo Ketone 12b:

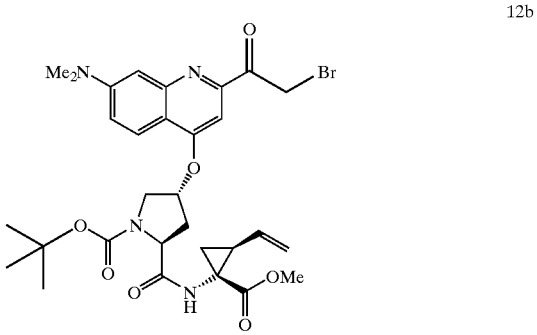

12b

Using the same procedure as described in Example 10 but using 2-carbomethoxy-7-dimethylamino-4- hydroxyquinoline (6b) for the synthesis of diester 11b, the title bromoketone 12b was obtained

Example 12

Permutation Library:

Both bromo ketones 12a and 12b were used in a permutation library for the parallel synthesis of compounds as shown in the following scheme V:

Scheme V

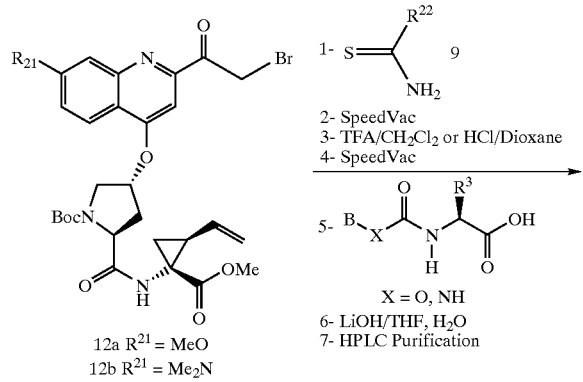

12a $R^{21}$ = MeO
12b $R^{21}$ = $Me_2N$

Step 1: Formation of the Aminothiazole Ring

A series of 8-mL vials were disposed in a reaction block from an ACT496 synthesizer (from Advanced Chemtech). In each vial was added the thiourea-$R^{22}$ of interest (0.055 mmol), the bromoketone (0.05 mmol, 31.63 mg OMe or 32.28 mg $NMe_2$) and isopropanol (500 μL) (see the diagram at the end for the position of each reactant in the block). The closed vials were heated at 70° C. for 1 h. The solvent was then evaporated using a vacuum centrifuge and was co-evaporated with 1,2-dichloroethane. The crude products were dried under high vacuum overnight.

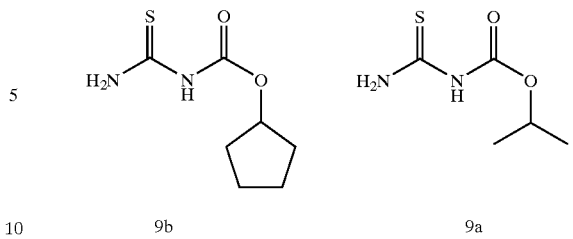

9b          9a

Step 2: Removal of the Boc Protecting Group

All the vials were treated with 30% TFA in DCM (500 μL) for 1 h. All vials were transferred on a vacuum centrifuge to remove the volatile material.

Step 3: Coupling

In each vial was added the corresponding carbamate and urea acid (0.07 mmol), HATU (0.07 mmol, 26.6 mg) and DIPEA (0.3 mmol, 50 μL) in 500 μL of DMSO and the reaction mixture was allowed to proceed overnight.

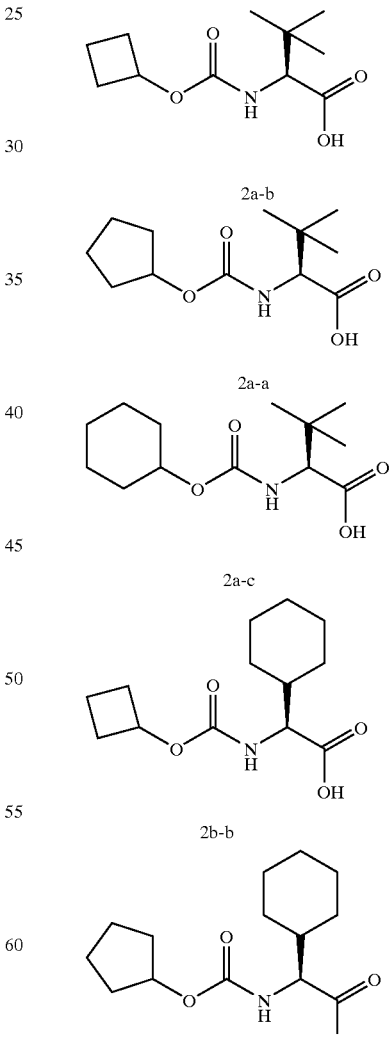

2a-b 2a-a 2a-c 2b-b 2b-a

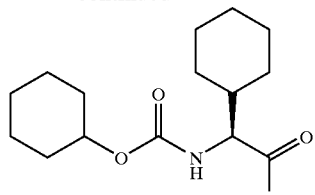

2b-c

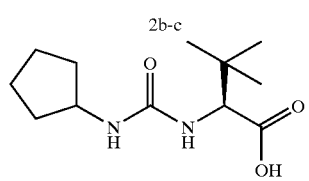

3a

Step 4: Saponification and Purification

All reactions were diluted with 400 μL of DMSO and 200 μL THF. A solution of 400 μL of aqueous 2N LiOH (0.8 mmol) was added to each vial and allowed to proceed overnight after which time, the mixture was neutralized by the addition of 400 μL of AcOH. All compounds were purified by semi-prep reversed-phase HPLC (Symmetry column 5 cm×19 cm, $CH_3CN/H_2O$ 0.06% TFA gradient).

Compound 108

Compound arising from combination of bromo ketone 12a, P3 fragment carbamate 2a–c and thiourea 9a:

Compound 108

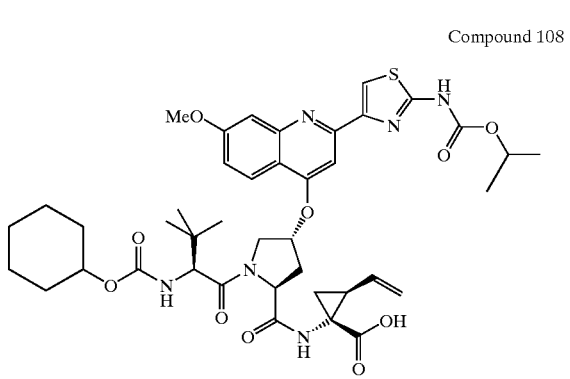

$^1$H NMR (400 MHz,DMSO-$d_6$): ca, 9:1 mixture of rotamers, major isomer description; δ 12.46 (br s, 1H), 12.00 (br s, 1H), 8.58 (s, 1H), 8.45–8.07 (m, 2H), 7.70–7.38 (m, 2H), 7.25–7.09 (m, 1H), 7.08 (d, J=8.0 Hz, 1H), 5.78–5.65 (m, 1H), 5.60–5.47 (m, 1H), 5.23–5.15 (m, 1H), 5.09–4.95 (m, 2H), 4.50–4.39 (m, 2H), 4.21–4.03 (m, 2H), 3.99–3.92 (m, 1H), 3.95 (s, 3H), 2.33–2.23 (m, 1H), 2.06–1.96 (m, 1H), 1.83–1.44 (m, 6H), 1.31 (d, J=6.0 Hz, 6H), 1.32–1.08 (m, 7H), 0.97 (s, 9H). M.S.(electrospray): 819.4 (M–H)$^-$ 821.3 (M+H)$^+$. Reverse Phase HPLC Homogeneity (0.06% TFA; $CH_3CN:H_2O$): 100%

Compound 109

Compound arising from combination of bromo ketone 12a, P3 fragment carbamate 2b–a and thiourea 9a:

Compound 109

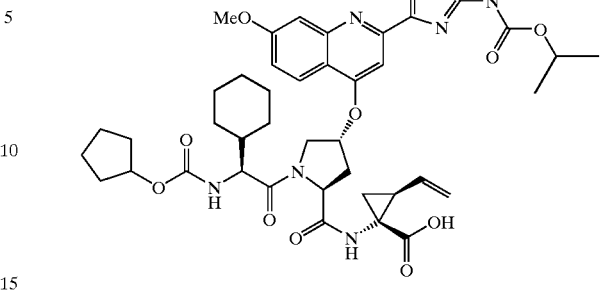

$^1$H NMR (400 MHz,DMSO-$d_6$): ca, 85:15 mixture of rotamers, major isomer description; δ 12.52 (br s, 1H), 11.99 (br s, 1H), 8.54 (s, 1H), 8.40–8.05 (m, 2H), 7.73–7.40 (m, 2H), 7.32–7.13 (m, 1H), 7.25 (d, J=7.9 Hz, 1H), 5.77–5.65 (m, 1H), 5.63–5.48 (m, 1H), 5.24–5.15 (m, 1H), 5.10–4.95 (m, 2H), 4.59–4.36 (m, 3H), 4.04–3.88 (m, 2H), 3.94 (s, 3H), 2.34–2.21 (m, 1H), 2.04–1.94 (m, 1H), 1.77–1.36 (m, 14H), 1.31 (d, J=6.0 Hz, 6H), 1.28–1.21 (m, 2H), 1.18–0.83 (m, 6H). M.S.(electrospray): 831.4 (M–H)$^-$ 833.4 (M+H)$^+$. Reverse Phase HPLC Homogeneity (0.06% TFA; $CH_3CN:H_2O$): 99%

Compound 115

Compound arising from combination of bromo ketone 12b, P3 fragment carbamate 2a–b and thiourea 9a:

Compound 115

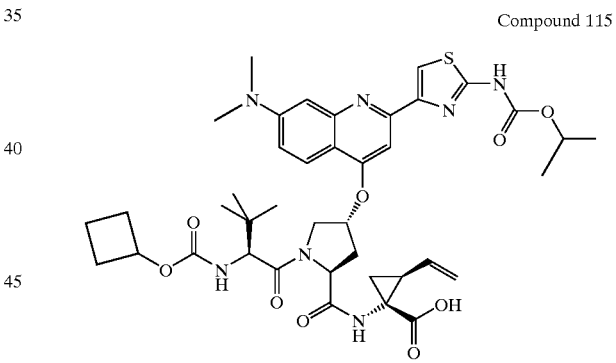

$^1$H NMR (400 MHz,DMSO-$d_6$): ca, 9:1 mixture of rotamers, major isomer description; δ 12.48 (br s, 1H), 12.08 (br s, 1H), 8.59 (s, 1H), 8.65–8.47 (m, 1H), 8.08 (d, J=9.1 Hz, 1H), 7.58–7.46 (m, 1H), 7.37–7.14 (m, 3H), 5.79–5.10 (m, 2H), 5.26–5.16 (m, 1H), 5.11–4.98 (m, 2H), 4.55–4.39 (m, 2H), 4.38–4.25 (m, 1H), 4.03–3.88 (m, 2H), 3.16 (s, 6H), 2.63–2.54 (m, 1H), 2.35–2.26 (m, 1H), 2.06–1.92 (m, 3H), 1.88–1.75 (m, 2H), 1.66–1.53 (m, 2H), 1.44–1.34 (m, 1H), 1.31 (d, J=6.3 Hz, 6H), 1.30–1.22 (m, 1H), 0.95 (s, 9H). M.S.(electrospray): 804.4 (M–H)$^-$ 806.4 (M+H)$^+$. Reverse Phase HPLC Homogeneity (0.06% TFA; $CH_3CN:H_2O$): 96%

Compound 202

Compound arising from combination of bromo ketone 12a, P3 fragment urea 3a and thiourea 9b:

Compound 202

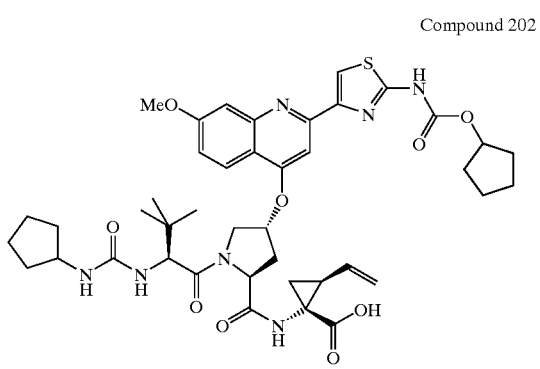

¹H NMR (400 MHz,DMSO-d₆): ca, 85:15 mixture of rotamers, major isomer description; δ 12.48 (br s, 1H), 12.00 (br s, 1H), 8.58 (s, 1H), 8.45–8.13 (m, 2H), 7.75–7.41 (m, 2H), 7.26–7.07 (m, 1H), 6.03 (d, J=6.6 Hz, 1H), 5.92 (d, J=9.6 Hz, 1H), 5.79–5.66 (m, 1H), 5.63–5.49 (m, 1H), 5.25–5.16 (m, 2H), 5.10–5.04 (m, 1H), 4.57–4.38 (m, 2H), 4.21–4.12 (m, 1H), 4.02–3.94 (m, 1H), 3.95 (s, 3H), 3.60–3.30 (m, under H2O, 1H), 2.35–2.23 (m, 1H), 2.07–1.98 (m, 1H), 1.97–1.85 (m, 2H), 1.80–1.36 (m, 14H), 1.30–1.02 (m, 3H), 0.95 (s, 9H). M.S.(electrospray): 830.4 (M−H)⁻ 832.4 (M+H)⁺. Reverse Phase HPLC Homogeneity (0.06% TFA; CH₃CN:H₂O): 100%

Compound 203

Compound arising from combination of bromo ketone 12b, P3 fragment urea 3a and thiourea 9a:

Compound 203

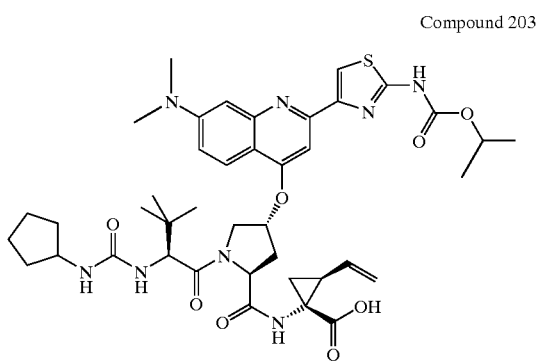

¹H NMR (400 MHz,DMSO-d₆): ca, 85:15 mixture of rotamers, major isomer description; δ 12.48 (br s, 1H), 12.08 (br s, 1H), 8.59 (s, 1H), 8.62–8.48 (m, 1H), 8.10 (d, J=9.2 Hz, 1H), 7.50 (br s, 1H), 7.27–7.12 (m, 2H), 6.01 (d, J=6.9 Hz, 1H), 5.89 (d, J=9.4 Hz, 1H), 5.78–5.57 (m, 2H), 5.26–5.16 (m, 1H), 5.11–4.97 (m, 2H), 4.61–4.51 (m, 1H), 4.48–4.39 (m, 1H), 4.17–4.08 (m, 1H), 4.02–3.94 (m, 1H), 3.55–3.25 (m, under H₂O, 1H), 3.14 (s, 6H), 2.37–2.26 (m, 1H), 2.16–1.98 (m, 1H), 1.81–1.21 (m, 9H), 1.31 (d, J=6.3 Hz, 6H), 1.19–1.00 (m, 2H), 0.945(s, 9H). M.S. (electrospray): 817.4 (M−H)⁻ 819.4 (M+H)⁺. Reverse Phase HPLC Homogeneity (0.06% TFA; CH₃CN:H₂O): 98%

Example 13

NS3–NS4A Protease Assay

The enzymatic assay used to evaluate the present compound is described in WO 00/09543 and WO 00/59929.

Example 14

Cell Based HCV RNA Replication Assay

Cell Culture

Huh7 cells that stably maintain a subgenomic HCV replicon were established as previously described (Lohman et al., 1999. Science 285: 110–113) and designated as the S22.3 cell-line. S22.3 cells are maintained in Dulbecco's Modified Earle Medium (DMEM) supplemented with 10% FBS and 1 mg/mL neomycin (Standard Medium). During the assay, DMEM medium supplemented with 10% FBS, containing 0.5% DMSO and lacking neomycin was used (Assay Medium). 16 hours prior to compound addition, S22.3 cells are trypsinized and diluted to 50 000 cells/mL in Standard Medium. 200 µL (10 000 cells) are distributed into each well of a 96-well plate. The plate was then incubated at 370 with 5% CO₂ until the next day.

| Reagents and Materials: | | | |
|---|---|---|---|
| Product | Company | Catalog # | Storage |
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bio-Whittaker | 14-901F | −20° C./4° C. |
| Neomycin (G418) | Gibco-BRL | 10131-027 | −20° C./4° C. |
| Trypsin-EDTA | Gibco-BRL | 25300-054 | −20° C./4° C. |
| 96-well plates | Costar | 3997 | RT |
| PVDF 0.22 µm Filter Unit | Millipore | SLGV025LS | RT |
| Deep-Well Titer Plate Polypropylene | Beckman | 267007 | RT |

Preparation of Test Compound

10 µL of test compound (in 100% DMSO) was added to 2 mL of Assay Medium for a final DMSO concentration of 0.5% and the solution was sonicated for 15 min and filtered through a 0.22 µM Millipore Filter Unit. 900 µL was transfered into row A of a Polypropylene Deep-Well Titer Plate. Rows B to H, contain 400 µL aliquots of Assay Medium (containing 0.5% DMSO), and are used to prepare serial dilutions (½) by transferring 400 µL from row to row (no compound was included in row H).

Application of Test Compound to Cells

Cell culture medium was aspirated from the 96-well plate containing the S22.3 cells. 175 µL of assay medium with the appropriate dilution of test compound was transferred from each well of the compound plate to the corresponding well of the cell culture plate (row H was used as the "No inhibition control"). The cell culture plate was incubated at 37° C. with 5% CO₂ for 72 h.

Extraction of Total Cellular RNA

Following the 72 h incubation period, the total cellular RNA was extracted from the S22.3 cells of the 96-well plate using the RNeasy 96 kit (Qiagen®, RNeasy Handbook. 1999.). Briefly, assay medium was completely removed from cells and 100 µL of RLT buffer (Qiagen®) containing 143 mM β-mercaptoethanol was added to each well of the 96-well cell-culture plate. The microplate was gently shaken for 20 sec. 100 µL of 70% ethanol was then added to each microplate well, and mixed by pipetting. The lysate was removed and applied to the wells of a RNeasy 96 (Qiagen®) plate that was placed on top of a Qiagen® Square-Well Block. The RNeasy 96 plate was sealed with tape and the Square-Well Block with the RNeasy 96 plate was loaded into the holder and placed in a rotor bucket of a 4K15C centrifuge. The sample was centrifuged at 6000 rpm (~5600×g) for 4 min at room temperature. The tape was removed from the plate and 0.8 mL of Buffer RW1 (Qiagen®) RNeasy 96 kit) was added to each well of the RNeasy 96 plate. The RNeasy 96 plate was sealed with a new piece of tape and centrifuged at 6000 rpm for 4 min at room temperature. The RNeasy 96 plate was placed on top of another clean Square-Well Block, the tape removed and 0.8 mL of Buffer RPE (Qiagen® RNeasy 96 kit) was added to each well of the RNeasy 96 plate. The RNeasy 96 plate was sealed with a new piece of tape and centrifuged at 6000 rpm for 4 min at room temperature. The tape was removed and another 0.8 mL of Buffer RPE (Qiagen® RNeasy 96 kit) was added to each well of the RNeasy 96 plate. The RNeasy 96 plate was sealed with a new piece of tape and centrifuged at 6000 rpm for 10 min at room temperature. Tape was removed, the RNeasy 96 plate was placed on top of a rack containing 1.2-mL collection microtubes. The RNA was eluted by adding 50 µL of RNase-free water to each well, sealing plate with a new piece of tape and incubated for 1 min at room temperature. The plate was then centrifuged at 6000 rpm for 4 min at room temperature. The elution step was repeated with a second volume of 50 µL RNase-free water. The microtubes with total cellular RNA are stored at −70°.

Quantification of Total Cellular RNA

RNA was quantified on the STORM® system (Molecular Dynamics®) using the RiboGreen® RNA Quantification Kit (Molecular Probes®). Briefly, the RiboGreen reagent was diluted 200-fold in TE (10 mM Tris-HCl pH=7.5, 1 mM EDTA). Generally, 50 µL of reagent was diluted in 10 mL TE. A Standard Curve of ribosomal RNA was diluted in TE to 2 µg/mL and pre-determined amounts (100, 50, 40, 20, 10, 5, 2 and 0 µL) of the ribosomal RNA solution are then transferred in a new 96-well plate (COSTAR # 3997) and the volume was completed to 100 µL with TE. Generally, column 1 of the 96-well plate was used for the standard curve and the other wells are used for the RNA samples to be quantified. 10 µL of each RNA sample that was to be quantified, was transferred to the corresponding well of the 96-well plate and 90 µL of TE was added. One volume (100/L) of diluted RiboGreen reagent was added to each well of the 96-well plate and incubated for 2 to 5 minutes at room temperature, protected from light (a 10 µL RNA sample in a 200 µL final volume generates a 20× dilution). The fluorescence intensity of each well was measured on the STORM® system (Molecular Dynamics®). A standard curve was created on the basis of the known quantities of the ribosomal RNA and the resulting fluorescent intensities. The RNA concentration in the experimental samples was determined from the standard curve and corrected for the 20× dilution.

Reagents and Materials:

| Product | Company | Catalog # | Storage |
|---|---|---|---|
| DEPC | Sigma | D5758 | 4° C. |
| EDTA | Sigma | E5134 | RT |
| Trizma-Base | Sigma | T8524 | RT |
| Trizma-HCl | Sigma | T7149 | RT |
| Collection Tube Strips | Qiagen | 19562 | RT |
| Ribogreen RNA Quantitation Kit | Molecular Probe | R11490 | −20° C. |
| Rneasy 96 Kit | Qiagen | 74183 | RT |
| Square-Well Blocks | Qiagen | 19573 | RT |

Real-Time RT-PCR

The Real-Time RT-PCR was performed on the ABI Prism 7700 Sequence Detection System using the TaqMan EZ RT-PCR Kit from (Perkin-Elmer Applied Biosystems®). RT-PCR was optimized for the quantification of the 5' IRES of HCV RNA by using the Taqman technology (Roche Molecular Diagnostics Systems) similar to the technique previously described (Martell et al., 1999. J. Clin. Microbiol. 37: 327–332). The system exploits the 5'-3' nucleolytic activity of AmpliTaq DNA polymerase. Briefly, the method utilizes a dual-labeled fluorogenic hybridization probe (PUTR Probe) that specifically anneals to the template between the PCR primers (primers 8125 and 7028). The 5' end of the probe contains a fluorescent reporter (6-carboxyfluorescein [FAM]) and the 3' end contains a fluorescent quencher (6-carboxytetramethylrhodamine [TAMRA]). The FAM reporter's emission spectrum was suppressed by the quencher on the intact hybridization probe. Nuclease degradation of the hybridization probe releases the reporter, resulting in an increase in fluorescence emission. The ABI Prism 7700 sequence detector measures the increase in fluorescence emission continuously during the PCR amplification such that the amplified product was directly proportion to the signal. The amplification plot was analysed early in the reaction at a point that represents the logarithmic phase of product accumulation. A point representing a defined detection threshold of the increase in the fluorescent signal associated with the exponential growth of the PCR product for the sequence detector was defined as the cycle threshold ($C_T$). $C_T$ values are inversely proportional to the quantity of input HCV RNA; such that under identical PCR conditions, the larger the starting concentration of HCV RNA, the lower the $C_T$. A standard curve was created automatically by the ABI Prism 7700 detection system by plotting the $C_T$ against each standard dilution of known HCV RNA concentration.

Reference samples for the standard curve are included on each RT-PCR plate. HCV Replicon RNA was synthesized (by T7 transcription) in vitro, purified and quantified by $OD_{260}$. Considering that 1 µg of this RNA=$2.15 \times 10^{11}$ RNA copies, dilutions are made in order to have $10^8$, $10^7$, $10^6$, $10^5$, $10^4$, $10^3$ or $10^2$ genomic RNA copies/5 µL. Total cellular Huh-7 RNA was also incorporated with each dilution (50 ng/5 µL). 5 µL of each reference standard (HCV Replicon+ Huh-7 RNA) was combined with 45 µL of Reagent Mix, and used in the Real-Time RT-PCR reaction.

The Real-Time RT-PCR reaction was set-up for the experimental samples that were purified on RNeasy 96-well plates by combining 5 µL of each total cellular RNA sample with 45 µL of Reagent Mix.

Reagents and Materials:

| Product | COMPANY | Catalog # | Storage |
|---|---|---|---|
| TaqMan EZ RT-PCR Kit | PE Applied Biosystems | N808-0236 | −20° C. |
| MicroAmp Optical Caps | PE Applied Biosystems | N801-0935 | RT |
| MicroAmp Optical 96-Well Reaction Plate | PE Applied Biosystems | N801-0560 | RT |

Reagent Mix preparation:

| Component | Volume for one sample (µL) | Volume for One Plate (µL) (91 samples + Dead Volume) | Final conc. |
|---|---|---|---|
| Rnase-free water | 16.5 | 1617 | |
| 5X TaqMan EZ buffer | 10 | 980 | 1X |
| Mn(OAc)$_2$ (25 mM) | 6 | 588 | 3 mM |
| dATP (10 mM) | 1.5 | 147 | 300 µM |
| dCTP (10 mM) | 1.5 | 147 | 300 µM |
| dGTP (10 mM) | 1.5 | 147 | 300 µM |
| dUTP (20 mM) | 1.5 | 147 | 600 µM |
| Forward Primer (10 µM) | 1 | 98 | 200 nM |
| Reverse Primer (10 µM) | 1 | 98 | 200 nM |
| PUTR probe (5 µM) | 2 | 196 | 200 nM |
| rTth DNA polymerase (2.5 U/µL) | 2 | 196 | 0.1 U/µL |
| AmpErase UNG (1 U/µL) | 0.5 | 49 | 0.01 U/µL |
| Total Volume | 45 | 4410 | |

```
Forward Primer Sequence                        (SEQ ID. 1):
5'-ACG CAG AAA GCG TCT AGC CAT GGC GTT AGT-3'

Reverse Primer Sequence                        (SEQ ID NO. 2):
5'-TCC CGG GGC ACT CGC AAG CAC CCT ATC AGG-3'
```

Note: Those primers amplify a region of 256-nt present within the 5' untranslated region of HCV.

PUTR Probe Sequence (SEQ ID NO. 3):

6FAM - TGG TCT GCG GAA CCG

GTG AGT ACA CC - TAMRA

No Template Controls (NTC): On each plate, 4 wells are used as "NTC". For these controls, 5 µL of water are added to the well in place of RNA.

Thermal Cycling Conditions:

| 50° C. | 2 min | |
|---|---|---|
| 60° C. | 30 min | |
| 95° C. | 5 min | |
| 95° C. | 15 sec | for 2 cycles |
| 60° C. | 1 min | |
| 90° C. | 15 sec | for 40 cycles |
| 60° C. | 1 min | |

Following the termination of the RT-PCR reaction the data analysis requires setting of threshold fluorescence signal for the PCR plate and a standard curve was constructed by plotting the $C_T$ value versus RNA copy number used in each reference reaction. The $C_T$ values obtained for the assay samples are used to interpolate an RNA copy number based on the standard curve. Finally, the RNA copy number was normalized (based on the RiboGreen RNA quantification of the total RNA extracted from the cell culture well) and expressed as genome equivalents/µg of total RNA [g.e./µg].

The RNA copy number [g.e./µg] from each well of the cell culture plate was a measure of the amount of replicating HCV RNA in the presence of various concentrations of inhibitor. The % inhibition was calculated with the following equation:

$$100-[(g.e./\mu g\ inh)/(g.e./\mu g\ ctl) \times 100].$$

A non-linear curve fit with the Hill model was applied to the inhibition-concentration data, and the 50% effective concentration ($EC_{50}$) was calculated by the use of SAS software (Statistical Software System; SAS Institute, Inc. Cary, N.C.).

When the compounds of this invention were evaluated in the preceding enzymatic and cell based assays, the compounds were found to be highly active. More specifically, the compounds had $IC_{50}$ values below 0.1 µM in the NS3–NS4A protease assay, and $EC_{50}$ values below 0.5 µM in the cell based HCV RNA replication assay.

Example 15

Specificity Assays

The specificity assays used to evaluate the selectivity of this compound are described in WO 00/09543.

When the compounds were evaluated in the specificity assays, the compounds of formula I were found to be selective in that they do not show significant inhibition in the Human Leukocyte Elastase and Cathepsin B assays.

Example 16

Pharmacokinetic Properties

The present compounds also show good pharmacokinetic properties such as detectable plasma levels in the rat at 1 hour and 2 h after an oral dose of 4 or 5 mg/kg.

More explicitly, the following assay, an in vivo oral absorption screen, was used to determine plasma levels of test compounds in a rat after oral administration:

Materials and Methods:

1. Method Used to Pool Compounds ("Cassette Selection"):

The selection of compounds to be pooled into a "cassette" was based on their structural similarity and physicochemical properties. A solid phase extraction method applicable to all the selected compounds was established. Based on the initial testing where each compound was spiked into rat plasma and run through HPLC or HPLC/MS at a concentration of 0.5 μM, the retention time, ionic mass, and the possible separation among compounds by HPLC and/or HPLC/MS were used as basis for pooling 3–4 compounds into one "cassette".

2. Oral Vehicle and Compound Preparation:

Each "cassette" contains 3–4 compounds at 5 or 4 mg/kg for each compound. The cassettes were prepared as an oral suspension in 0.5% aqueous methylcellulose and 0.3% of polyoxyethylene (20) sorbitan monooleate (Tween-80). The dosing volume was 10 mL/kg via oral gavage.

3. Dosing and Plasma Sampling:

Male Sprague Dawley rats were fasted overnight in individual cages, with access to aqueous 10% dextrose. Two rats were dosed with each "cassette". Plasma samples (~1 mL) were collected at 1 and 2 h post-dosing from the 2 rats and pooled for extraction and analysis.

4. Compound Extraction and Analysis:

From each cassette, plasma samples at 1 and 2 h, blank plasma, blank plasma spiked with all the compounds at 0.5 μM of each, are extracted by the solid phase extraction method. Samples were analyzed by HPLC and HPLC/MS for comparison purpose. Plasma concentrations are estimated based on the single concentration of 0.5 μM standard.

Results

When assayed in the preceding screen, compounds of this invention were found to present levels in the plasma at the 1 hour and 2 hour intervals following oral administration, achieving blood plasma levels up to 0.5 μM and 0.6 μM respectively.

TABLE 1

| Cpd | B | R³ | R²¹ | R²² | R^C | m/z (M + H)⁺ |
|---|---|---|---|---|---|---|
| 101 | cyclopentylmethyl | tBu | —OCH₃ | —NHC(O)O-isobutyl | —OH | 821.4 |
| 102 | cyclopentylmethyl | tBu | —OCH₃ | —NHC(O)OMe | —OH | 779.2 |
| 103 | cyclopentylmethyl | tBu | —OCH₃ | —NHC(O)NHEt | —OH | 672.2 |
| 104 | cyclopentylmethyl | tBu | —OCH₃ | —NHC(O)O-cyclopentyl | —OH | 833.4 |

TABLE 1-continued

| Cpd | B | R³ | R²¹ | R²² | R^C | m/z (M + H)⁺ |
|---|---|---|---|---|---|---|
| 105 | cyclopentyl | tert-butyl | —OCH₃ | NH-C(O)O-isopropyl | —OH | 807.3 |
| 106 | cyclobutyl | tert-butyl | —OCH₃ | NH-C(O)O-cyclopentyl | —OH | 819.4 |
| 107 | cyclobutyl | tert-butyl | —OCH₃ | NH-C(O)O-isopropyl | —OH | 793.4 |
| 108 | cyclohexyl | tert-butyl | —OCH₃ | NH-C(O)O-isopropyl | —OH | 821.3 |
| 109 | cyclopentyl | cyclohexyl | —OCH₃ | NH-C(O)O-isopropyl | —OH | 833.4 |
| 110 | cyclohexyl | cyclohexyl | —OCH₃ | NH-C(O)O-isopropyl | —OH | 847.4 |
| 111 | cyclohexyl | tert-butyl | —OCH₃ | NH-C(O)O-cyclopentyl | —OH | 847.4 |

TABLE 1-continued

| Cpd | B | R³ | R²¹ | R²² | R^C | m/z (M + H)⁺ |
|---|---|---|---|---|---|---|
| 112 | cyclobutyl | cyclohexyl | —OCH₃ | NHC(O)O-cyclopentyl | —OH | 845.4 |
| 113 | cyclopentyl | cyclohexyl | —OCH₃ | NHC(O)O-cyclopentyl | —OH | 859.4 |
| 114 | cyclohexyl | cyclohexyl | —OCH₃ | NHC(O)O-cyclopentyl | —OH | 873.4 |
| 115 | cyclobutyl | tert-butyl | N(CH₃)₂ | NHC(O)O-isopropyl | —OH | 806.4 |
| 116 | cyclopentyl | tert-butyl | N(CH₃)₂ | NHC(O)O-isopropyl | —OH | 820.4 |
| 117 | cyclohexyl | tert-butyl | N(CH₃)₂ | NHC(O)O-isopropyl | —OH | 834.4 |
| 118 | cyclobutyl | cyclohexyl | N(CH₃)₂ | NHC(O)O-isopropyl | —OH | 832.4 |

TABLE 1-continued

| Cpd | B | R³ | R²¹ | R²² | R^C | m/z (M + H)⁺ |
|---|---|---|---|---|---|---|
| 119 | cyclopentyl | cyclohexyl | N(CH₃)₂ | NH-C(O)-O-isopropyl | —OH | 846.4 |
| 120 | cyclohexyl | cyclohexyl | N(CH₃)₂ | NH-C(O)-O-isopropyl | —OH | 860.4 |
| 121 | cyclobutyl | tert-butyl | N(CH₃)₂ | NH-C(O)-O-cyclopentyl | —OH | 832.4 |
| 122 | cyclopentyl | tert-butyl | N(CH₃)₂ | NH-C(O)-O-cyclopentyl | —OH | 846.4 |
| 123 | cyclohexyl | tert-butyl | N(CH₃)₂ | NH-C(O)-O-cyclopentyl | —OH | 860.4 |
| 124 | cyclobutyl | cyclohexyl | N(CH₃)₂ | NH-C(O)-O-cyclopentyl | —OH | 858.4 |
| 125 | cyclopentyl | cyclohexyl | N(CH₃)₂ | NH-C(O)-O-cyclopentyl | —OH | 872.4 |

TABLE 1-continued

| Cpd | B | R³ | R²¹ | R²² | R^C | m/z (M + H)⁺ |
|---|---|---|---|---|---|---|
| 126 | cyclohexylmethyl | cyclohexyl | N(CH₃)₂ | cyclopentyl carbamate | —OH | 886.5 |
| 127 | cyclopentylmethyl | tert-butyl | N(CH₃)₂ | cyclopentyl carbamate | —OH | 845.4 |

TABLE 2

| Cpd | B | R³ | R²¹ | R²² | R^C | m/z (M + H)⁺ |
|---|---|---|---|---|---|---|
| 201 | cyclopentylmethyl | tert-butyl | —OCH₃ | isopropyl carbamate | —OH | 806.3 |

TABLE 2-continued

| Cpd | B | R³ | R²¹ | R²² | Rᶜ | m/z (M + H)⁺ |
|---|---|---|---|---|---|---|
| 202 | cyclopentylmethyl | t-Bu | —OCH₃ | carbamate-O-cyclopentyl | —OH | 832.4 |
| 203 | cyclopentylmethyl | t-Bu | —N(CH₃)₂ | carbamate-O-isopropyl | —OH | 819.4 |

---

What is claimed is:

1. A racemate, diastereoisomer, or optical isomer of a compound of formula (I):

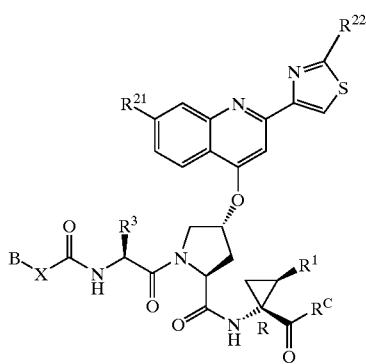

wherein B is $(C_{1-10})$alkyl, $(C_{3-7})$cycloalkyl, or $(C_{1-4})$alkyl-$(C_{3-7})$cycloalkyl,
  a) wherein said cycloalkyl and alkyl-cycloalkyl may be mono-, di- or tri-substituted with $(C_{1-3})$alkyl; and
  b) wherein said alkyl, cycloalkyl, and alkyl-cycloalkyl may be mono- or di-substituted with substituents selected from hydroxy and O—$(C_{1-4})$alkyl; and
  c) wherein each of said alkyl groups may be mono-, di- or tri-substituted by halogen; and
  d) wherein in each of said cycloalkyl groups being 5-, 6- or 7-membered, one or two —CH$_2$-groups not being directly linked to each other may be replaced by —O— such that the O-atom is linked to the group X via at least two C-atoms;

X is O or NH;

$R^3$ is $(C_{2-8})$alkyl, $(C_{3-7})$cycloalkyl, or $(C_{1-3})$alkyl-$(C_{3-7})$cycloalkyl, wherein each of said alkyl and cycloalkyl groups may be mono-, di- or tri-substituted with $(C_{1-4})$alkyl;

$R^{21}$ is H, halogen, —OH, $(C_{1-6})$alkyl, $(C_{3-6})$cycloalkyl, —$(C_{1-4})$alkyl-$(C_{3-6})$cycloalkyl, $(C_{1-6})$alkoxy, —O—$(C_{3-6})$cycloalkyl, —O—$(C_{1-4})$alkyl-$(C_{3-6})$cycloalkyl or —N$(R^{24})_2$, wherein each $R^{24}$ is independently: H, $(C_{1-6})$alkyl, —$(C_{3-6})$cycloalkyl, or —$(C_{1-4})$alkyl-$(C_{3-6})$cycloalkyl;

$R^{22}$ is NR$^{N2}$COOR$^O$ or —NR$^{N2}$CONR$^{N3}$R$^{N1}$, wherein
  $R^O$ is selected from $(C_{1-8})$alkyl, $(C_{3-7})$cycloalkyl, and $(C_{1-4})$alkyl-$(C_{3-7})$cycloalkyl, wherein said cycloalkyl and alkyl-cycloalkyl may be mono-, di- or tri-substituted with $(C_{1-3})$alkyl;
  $R^{N1}$ is H or $R^O$ as defined above; and
  $R^{N2}$ and $R^{N3}$ are independently selected from H and methyl;

$R^1$ is ethyl or vinyl;

$R^c$ is hydroxy or NHSO$_2$R$^S$ wherein $R^S$ is $(C_{1-6})$alkyl, $(C_{3-7})$cycloalkyl or $(C_{1-6})$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; each of which optionally being mono-, di- or tri-substituted with substituents selected from halogen, hydroxy, cyano, $(C_{1-4})$alkyl, O—$(C_{1-6})$alkyl, —CO—NH$_2$, —CO—NH$((C_{1-4})$alkyl), —CO—N$((C_{1-4})$alkyl)$_2$, —NH$_2$, —NH$((C_{1-4})$alkyl), —N$((C_{1-4})$alkyl)$_2$, wherein $(C_{1-4})$alkyl and O—$(C_{1-6})$alkyl are optionally mono-, di- or trisubstituted with halogen; and each of which optionally being monosubstituted with nitro;

or a pharmaceutically acceptable salt or ester thereof.

2. The compound according to claim 1, wherein

B is $(C_{1-10})$alkyl, $(C_{3-7})$cycloalkyl or $(C_{1-4})$alkyl-$(C_{3-7})$cycloalkyl,
  a) wherein said cycloalkyl and alkyl-cycloalkyl may be mono-, di- or tri-substituted with $(C_{1-3})$alkyl; and
  b) wherein said alkyl, cycloalkyl and alkyl-cycloalkyl may be mono- or di-substituted with substituents selected from hydroxy and O—$(C_{1-4})$alkyl; and
  c) wherein each of said alkyl-groups may be mono-, di- or tri-substituted by halogen; and
  d) wherein in each of said cycloalkyl-groups being 5-, 6- or 7-membered, one or two —CH$_2$-groups not being directly linked to each other may be replaced by —O— such that the O-atom is linked to the group X via at least two C-atoms;

X is O or NH;

$R^3$ is $(C_{2-8})$alkyl, $(C_{3-7})$cycloalkyl or $(C_{1-3})$alkyl-$(C_{3-7})$cycloalkyl, wherein said cycloalkyl groups may be mono-, di- or tri-substituted with $(C_{1-4})$alkyl;

$R^{21}$H, halogen, —OH, $(C_{1-6})$alkyl, $(C_{3-6})$cycloalkyl, —$(C_{1-4})$alkyl-$(C_{3-6})$cycloalkyl, $(C_{1-6})$alkoxy, —O—$(C_{3-6})$cycloalkyl, —O—$(C_{1-4})$alkyl-$(C_{3-6})$cycloalkyl or —N$(R^{24})_2$, wherein each $R^{24}$ is independently: H, $(C_{1-6})$alkyl, —$(C_{3-6})$cycloalkyl, or —$(C_{1-4})$alkyl-$(C_{3-6})$cycloalkyl;

$R^{22}$ is —NR$^{N2}$COOR$^O$ or —NR$^{N2}$CONR$^{N3}$R$^{N1}$ wherein
  $R^O$ is selected from $(C_{1-8})$alkyl, $(C_{3-7})$cycloalkyl and $(C_{1-4})$alkyl-$(C_{3-7})$cycloalkyl, wherein said cycloalkyl, alkyl-cycloalkyl may be mono-, di- or tri-substituted with $(C_{1-3})$alkyl;
  $R^{N1}$ is H or $R^O$ as defined above; and
  $R^{N2}$ and $R^{N3}$ are independently selected from H and methyl;

$R^1$ is ethyl or vinyl;

$R^c$ is hydroxy or NHSO$_2$R$^S$ wherein $R^S$ is $(C_{1-6})$alkyl, $(C_{3-7})$cycloalkyl or $(C_{1-6})$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; all of which optionally being mono-, di- or tri-substituted with substituents selected from halogen, hydroxy, cyano, $(C_{1-4})$alkyl, O—$(C_{1-6})$alkyl, —CO—NH$_2$, —CO—NH$((C_{1-4})$alkyl), —CO—N$((C_{1-4})$alkyl)$_2$, —NH$_2$, —NH$((C_{1-4})$alkyl), —N$((C_{1-4})$alkyl)$_2$; and all of which optionally being monosubstituted with nitro;

or a pharmaceutically acceptable salt or ester thereof.

3. The compound according to claim 1, wherein $R^{21}$ is selected from halogen, —OH, $(C_{1-3})$alkoxy or N$(R^{24})_2$, wherein each $R^{24}$ is independently: H or $(C_{1-6})$alkyl.

4. The compound according to claim 3, wherein $R^{21}$ is selected from —OH, —OCH$_3$ and —N(CH$_3$)$_2$.

5. The compound according to claim 1, wherein $R^{22}$ is —NHCOOR⁰ or —NHCONHR^{N1}, wherein $R^{N1}$ and R⁰ are defined as in claim 1.

6. The compound according to claim 5, wherein R⁰ and $R^{N1}$, are selected from the group consisting of methyl, ethyl, propyl, 1-methylethyl, butyl, 1-methylpropyl, 2-methylpropyl, 1,1-dimethylethyl, cyclopropyl, cyclobutyl, cyclopentyl, cyclohexyl, cyclopropylmethyl, cyclobutylmethyl, cyclopentylmethyl and cyclohexylmethyl; wherein said cycloalkyl and alkyl-cycloalkyl groups optionally being substituted by 1 to 3 substituents selected from methyl and ethyl.

7. The compound according to claim 1, wherein B is selected from $(C_{1-4})$alkyl, $(C_{3-7})$cycloalkyl and $(C_{1-3})$alkyl-$(C_{3-7})$cycloalkyl,
 a) wherein said cycloalkyl and alkyl-cycloalkyl may be mono-, di- or tri-substituted with $(C_{1-3})$alkyl; and
 b) wherein said alkyl, cycloalkyl and alkyl-cycloalkyl may be mono- or di-substituted with substituents selected from hydroxy and O—$(C_{1-4})$alkyl; and
 c) wherein each of said alkyl groups may be mono-, di- or tri-substituted with fluorine or mono-substituted by chlorine or bromine; and
 d) wherein in each of said cycloalkyl groups being 5-, 6- or 7-membered, one or two —CH₂-groups not being directly linked to each other may be replaced by —O— such that the O-atom is linked to the group X via at least two C-atoms.

8. The compound according to claim 7, wherein B is selected from ethyl, n-propyl, i-propyl, n-butyl, 1-methylpropyl, 2-methylpropyl, tert-butyl, cyclopropyl, cyclobutyl, cyclopentyl, cyclohexyl, cyclopropylmethyl, cyclobutylmethyl, cyclopentylmethyl and cyclohexylmethyl,
 a) wherein each of said cycloalkyl and alkyl-cycloalkyl groups optionally being substituted by 1 to 3 substituents selected from methyl and ethyl;
 b) wherein each of said groups optionally being mono- or di-substituted with substituents selected from hydroxy, methoxy and ethoxy; and
 c) wherein each of said alkyl groups may be mono-, di- or tri-substituted with fluorine or mono-substituted by chlorine or bromine and
 d) wherein in each of said cycloalkyl-groups being 5-, 6- or 7-membered, one or two —CH₂-groups not being directly linked to each other may be replaced by —O— such that the O-atom is linked to the group X via at least two C-atoms.

9. The compound according to claim 8, wherein B is selected from cyclopropyl, cyclobutyl, cyclopentyl, cyclohexyl, 1-methylcyclopentyl and 1-methylcyclohexyl.

10. The compound according to claim 1, wherein R³ is selected from ethyl, propyl, butyl, cyclopropyl, cyclobutyl, cyclopentyl, cyclohexyl, cyclopropylmethyl, cyclobutylmethyl, cyclopentylmethyl, cyclohexylmethyl, each of which optionally being substituted by 1 to 3 substituents selected from methyl, ethyl and propyl.

11. The compound according to claim 10, wherein R³ is selected from 1-methylethyl, 1,1-dimethylethyl, 1-methylpropyl, 2-methylpropyl, 1,1-dimethylpropyl, 1,2-dimethylpropyl, 2,2-dimethylpropyl, cyclopentyl, cyclohexyl, 1-methylcyclopentyl, 1-methylcyclohexyl, cyclopentylmethyl, cyclohexylmethyl, (1-methylcyclopentyl)methyl and (1-methylcyclohexyl)methyl.

12. The compound according to claim 1, wherein R¹ is vinyl.

13. The compound according to claim 1, wherein $R^c$ is selected from hydroxy or $NHSO_2R^S$ wherein $R^S$ is methyl, ethyl, n-propyl, i-propyl, n-butyl, 1-methylpropyl, 2-methylpropyl, tert-butyl, cyclopropyl, cyclobutyl, cyclopentyl, cyclohexyl, cyclopropylmethyl, cyclobutylmethyl, cyclopentylmethyl, cyclohexylmethyl, phenyl, naphthyl, pyridinyl, phenylmethyl, naphthylmethyl or pyridinylmethyl,
 a) each of which optionally being mono-, di- or tri-substituted with substituents selected from fluorine and methyl; and
 b) each of which optionally being mono- or disubstituted with substituents selected from hydroxy, trifluoromethyl, methoxy and trifluoromethoxy; and
 c) each of which optionally being monosubstituted with substituents selected from chlorine, bromine, cyano, nitro, —CO—NH₂, —CO—NHCH₃, —CO—N(CH₃)₂, —NH₂, —NH(CH₃) and —N(CH₃)₂.

14. The compound according to claim 13 wherein $R^c$ is hydroxy, NHSO₂-methyl, NHSO₂-ethyl, NHSO₂-(1-methyl)ethyl, NHSO₂-propyl, NHSO₂-cyclopropyl, NHSO₂-cyclopropylmethyl, NHSO₂-cyclobutyl, NHSO₂-cyclopentyl or NHSO₂-phenyl.

15. The compound according to claim 14 wherein the group $R^c$ is hydroxy.

16. The compound according to claim 14 wherein the group $R^c$ is NHSO₂-cyclopropyl.

17. The compound according to claim 1, wherein X is O.

18. The compound according to claim 1, wherein X is NH.

19. The compound according to claim 1, represented by formula:

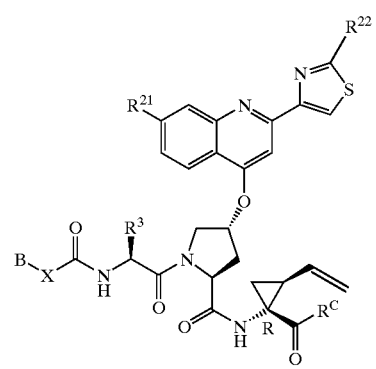

wherein $R^{21}$ is —OCH₃ or N(CH₃)₂;

$R^{22}$ is —NHCOOR⁰ or —NHCONHR^{N1}, wherein R⁰ and $R^{N1}$ is each independently selected from $(C_{1-4})$alkyl or $(C_{3-6})$cycloalkyl;

B is $(C_{4-6})$cycloalkyl;

X is O or NH;

$R^3$ is tert-butyl or cyclohexyl;

$R^c$ is hydroxy or $NHSO_2R^S$ wherein $R^S$ is $(C_{1-4})$alkyl, $(C_{3-6})$cycloalkyl or phenyl;

or a pharmaceutically acceptable salt or ester thereof.

20. The compound according to claim 19, wherein $R^{21}$ is —$OCH_3$; $R^{22}$ is —$NHCOOR^0$ wherein $R^0$ is isopropyl or cyclopentyl; and $R^c$ is $NHSO_2R^S$ wherein $R^S$ is cyclopropyl; and wherein B, X, $R^{22}$, and $R^3$ are defined as in claim 19.

21. The compound according to claim 19 wherein $R^c$ is hydroxy and wherein B, X, $R^{21}$, $R^{22}$, and $R^3$ are defined as in claim 19.

22. The compound according to claim 21 wherein $R^{21}$ is —$OCH_3$ and $R^{22}$ is —$NHCOOR^0$ wherein $R^0$ is isopropyl or cyclopentyl, and wherein B, X, $R^c$, and $R^3$ are defined as in claim 21.

23. The compound according to claim 1 of the formula

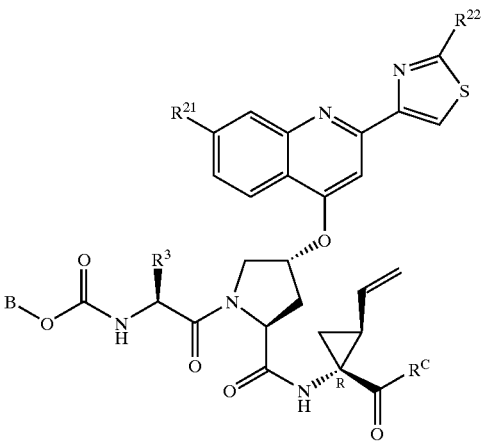

wherein the substituents B, $R^3$, $R^{21}$, $R^{22}$ and $R^c$ are defined according to the following table -continued

| Cpd | B | R³ | R²¹ | R²² | R^C |
|---|---|---|---|---|---|
| 108 | cyclohexyl | t-butyl | —OCH₃ | —NHC(O)O-iPr | —OH |
| 109 | cyclopentyl | cyclohexyl | —OCH₃ | —NHC(O)O-iPr | —OH |
| 110 | cyclohexyl | cyclohexyl | —OCH₃ | —NHC(O)O-iPr | —OH |
| 111 | cyclohexyl | t-butyl | —OCH₃ | —NHC(O)O-cyclopentyl | —OH |
| 112 | cyclobutyl | cyclohexyl | —OCH₃ | —NHC(O)O-cyclopentyl | —OH |
| 113 | cyclopentyl | cyclohexyl | —OCH₃ | —NHC(O)O-cyclopentyl | —OH |
| 114 | cyclohexyl | cyclohexyl | —OCH₃ | —NHC(O)O-cyclopentyl | —OH |
| 115 | cyclobutyl | t-butyl | —N(CH₃)₂ | —NHC(O)O-iPr | —OH |
| 116 | cyclopentyl | t-butyl | —N(CH₃)₂ | —NHC(O)O-iPr | —OH |
| 117 | cyclohexyl | t-butyl | —N(CH₃)₂ | —NHC(O)O-iPr | —OH |

-continued

| Cpd | B | R³ | R²¹ | R²² | Rᶜ |
|---|---|---|---|---|---|
| 118 | cyclobutyl | cyclohexyl | N(CH₃)₂ | NHC(O)O-iPr | —OH |
| 119 | cyclopentyl | cyclohexyl | N(CH₃)₂ | NHC(O)O-iPr | —OH |
| 120 | cyclohexyl | cyclohexyl | N(CH₃)₂ | NHC(O)O-iPr | —OH |
| 121 | cyclobutyl | C(CH₃)₂ | N(CH₃)₂ | NHC(O)O-cyclopentyl | —OH |
| 122 | cyclopentyl | C(CH₃)₂ | N(CH₃)₂ | NHC(O)O-cyclopentyl | —OH |
| 123 | cyclohexyl | C(CH₃)₂ | N(CH₃)₂ | NHC(O)O-cyclopentyl | —OH |
| 124 | cyclobutyl | cyclohexyl | N(CH₃)₂ | NHC(O)O-cyclopentyl | —OH |
| 125 | cyclopentyl | cyclohexyl | N(CH₃)₂ | NHC(O)O-cyclopentyl | —OH |
| 126 | cyclohexyl | cyclohexyl | N(CH₃)₂ | NHC(O)O-cyclopentyl | —OH |
| 127 | cyclopentyl | C(CH₃)₂ | N(CH₃)₂ | NHC(O)O-cyclopentyl | —OH |

24. The compound according to claim 1 of the formula

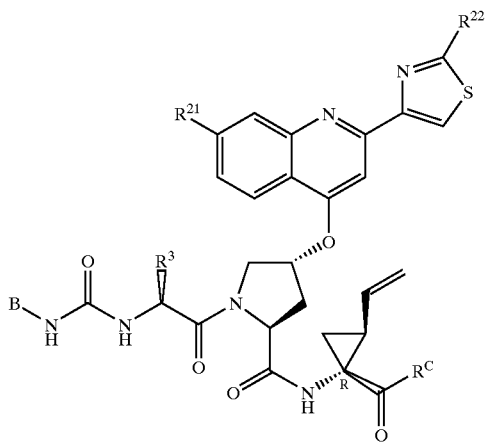

wherein the substituents B, $R^3$, $R^{21}$, $R^{22}$ and $R^c$ are defined according to the following table

| Cpd | B | $R^3$ | $R^{21}$ | $R^{22}$ | $R^C$ |
|---|---|---|---|---|---|
| 201 | cyclopentylmethyl | tert-butyl | —OCH$_3$ | NH-C(O)-O-iPr | —OH |
| 202 | cyclopentylmethyl | tert-butyl | —OCH$_3$ | NH-C(O)-O-cyclopentyl | —OH |
| 203 | cyclopentylmethyl | tert-butyl | —N(CH$_3$)$_2$ | NH-C(O)-O-iPr | —OH |

25. A pharmaceutical composition comprising an anti-hepatitis C virally effective amount of a compound of formula I according to claim 1 or a pharmaceutically acceptable salt or ester thereof, in admixture with at least one pharmaceutically acceptable carrier medium or auxiliary agent.

26. The pharmaceutical composition according to claim 25 further comprising a therapeutically effective amount of at least one other antiviral agent.

27. The pharmaceutical composition according to claim 26, wherein said other antiviral agent is ribavirin.

28. The pharmaceutical composition according to claim 26, wherein said other antiviral agent is selected from another anti-HCV agent, HIV inhibitor, HAV inhibitor and HBV inhibitor.

29. The pharmaceutical composition according to claim 28 wherein said other anti-HCV agent is selected from immunomodulatory agents, other inhibitors of HCV NS3 protease, inhibitors of HCV polymerase and inhibitors of another target in the HCV life cycle.

30. The pharmaceutical composition according to claim 29 wherein said immunomodulatory agent is selected from α-interferon and pegylated α-interferon.

31. The pharmaceutical composition according to claim 29, wherein said inhibitor of another target in the HCV life cycle is selected from inhibitors of: helicase, NS2/3 protease and internal ribosome entry site (IRES).

32. A method for the treatment of a hepatitis C viral infection in a mammal by administering to the mammal an anti-hepatitis C virally effective amount of a compound of formula I according to claim 1, or a pharmaceutically acceptable salt or ester thereof.

33. A method for the treatment of a hepatitis C viral infection in a mammal by administering thereto an anti-hepatitis C virally effective amount of a compound of formula I according to claim 1, or a pharmaceutically acceptable salt or ester thereof, in combination with at least one other antiviral agent.

34. The method according to claim 33, wherein said antiviral agent is ribavirin.

35. The method according to claim 33, wherein said other antiviral agent is selected from another anti-HCV agent, HIV inhibitor, HAV inhibitor and HBV inhibitor.

36. The method according to claim 35, wherein said other anti-HCV agent is selected from immunomodulatory agents, other inhibitors of HCV NS3 protease, inhibitors of HCV polymerase and inhibitors of another target in the HCV life cycle.

37. The method according to claim 36, wherein said immunomodulatory agent is selected from α-interferon and pegylated α-interferon.

38. The method according to claim 36, wherein said inhibitor of another target in the HCV life cycle is selected from inhibitors of: helicase, NS2/3 protease and internal ribosome entry site (IRES).

* * * * *

SEQUENCE LISTING

<160> NUMBER OF SEQ ID NOS: 3

<210> SEQ ID NO 1
<211> LENGTH: 30
<212> TYPE: DNA
<213> ORGANISM: Artificial
<220> FEATURE:
<223> OTHER INFORMATION: Forward primer

<400> SEQUENCE: 1
acgcagaaag cgtctagcca tggcgttagt                30

<210> SEQ ID NO 2
<211> LENGTH: 30
<212> TYPE: DNA
<213> ORGANISM: Artificial
<220> FEATURE:
<223> OTHER INFORMATION: Reverse primer

<400> SEQUENCE: 2
tcccggggca ctcgcaagca ccctatcagg                30

<210> SEQ ID NO 3
<211> LENGTH: 26
<212> TYPE: DNA
<213> ORGANISM: Artificial
<220> FEATURE:
<223> OTHER INFORMATION: PUTR probe

```
<400> SEQUENCE: 3
tggtctgcgg aaccggtgag tacacc                                    26
```